US008273749B2

(12) United States Patent
Duffy et al.

(10) Patent No.: US 8,273,749 B2
(45) Date of Patent: Sep. 25, 2012

(54) N-SUBSTITUTED OXINDOLINE DERIVATIVES AS CALCIUM CHANNEL BLOCKERS

(75) Inventors: Joseph L. Duffy, Cranford, NJ (US); Scott B. Hoyt, Hoboken, NJ (US); Clare London, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 34 days.

(21) Appl. No.: 12/678,357

(22) PCT Filed: Sep. 30, 2008

(86) PCT No.: PCT/US2008/011290
§ 371 (c)(1),
(2), (4) Date: Mar. 16, 2010

(87) PCT Pub. No.: WO2009/045386
PCT Pub. Date: Apr. 9, 2009

(65) Prior Publication Data
US 2010/0216815 A1  Aug. 26, 2010

Related U.S. Application Data

(60) Provisional application No. 60/997,624, filed on Oct. 4, 2007.

(51) Int. Cl.
*A61K 31/4015* (2006.01)
*C07D 209/34* (2006.01)
*C07D 241/14* (2006.01)
*C07D 401/04* (2006.01)

(52) U.S. Cl. .................. 514/255.05; 514/339; 514/418; 544/336; 546/277.7; 548/486

(58) Field of Classification Search .................. 548/486
See application file for complete search history.

(56) References Cited

U.S. PATENT DOCUMENTS

| | | | |
|---|---|---|---|
| 5,393,732 A | 2/1995 | Cox et al. | |
| 5,618,720 A | 4/1997 | Ellis et al. | |
| 5,686,241 A | 11/1997 | Ellis et al. | |
| 5,710,250 A | 1/1998 | Ellis et al. | |
| 5,726,035 A | 3/1998 | Jay et al. | |
| 5,792,846 A | 8/1998 | Harpold et al. | |
| 5,846,757 A | 12/1998 | Harpold et al. | |
| 5,851,824 A | 12/1998 | Harpold et al. | |
| 5,874,236 A | 2/1999 | Harpold et al. | |
| 5,876,958 A | 3/1999 | Harpold et al. | |
| 6,013,474 A | 1/2000 | Ellis et al. | |
| 6,057,114 A | 5/2000 | Akong et al. | |
| 6,096,514 A | 8/2000 | Harpold et al. | |
| 6,462,032 B1 | 10/2002 | Grubb et al. | |
| 6,608,068 B2 | 8/2003 | Fensome et al. | |
| 7,084,168 B2 | 8/2006 | Fensome et al. | |
| 7,253,203 B2 | 8/2007 | Fensome et al. | |
| 2006/0252758 A1 | 11/2006 | Chafeev et al. | |
| 2006/0252812 A1 | 11/2006 | Chafeev et al. | |
| 2006/0258659 A1 | 11/2006 | Chafeev et al. | |
| 2007/0105820 A1 | 5/2007 | Chafeev et al. | |

FOREIGN PATENT DOCUMENTS

| | | |
|---|---|---|
| WO | WO8603749 | 7/1986 |
| WO | WO9106545 | 4/1991 |
| WO | WO9104974 | 5/1991 |
| WO | WO9928342 | 6/1999 |
| WO | WO2006/098969 | 9/2006 |
| WO | WO2009045381 | 4/2009 |

OTHER PUBLICATIONS

Chronic pain [online] retrieved from the internet on Jul. 2, 2011. URL; http://www.emedicinehealth.com/script/main/art.asp?articlekey=59398&pf=3&page=4.*
W. A. Catterall et al., "Structure and Regulation of Voltage-Gated Ca2+ Channels", vol. 16, pp. 521-555, 2000, Annu. Rev. Cell Dev. Biol.
G. H. Hockerman et al., "Construction of a Hig-Affinity Receptor Site for Dihydropyridine Agonists and Antagonists by Single Amino Acid Substitutions in a Non-L-Type CA2+ Channel" vol. 94, pp. 14906-14911, 1997, Proc. Natl. Acad. Sci.
P. S. Staats et al., "Intrathecal Ziconotide in the Treatment of Refractory Pain in Patients with Cancer or AIDS", vol. 291, pp. 63-70, 2004, JAMA.
F. Colburne et al, "Continuing Postischemic Neuronal Death in CA1, Influence of Ischemia Duration and Cytoprotective Doses of NBQX ad SNX-111 in Rats", 1999, vol. 30, pp. 662-668, Stroke.
J. E. McRory et al., "Molecular and Functional Characterization of a Family of Rat Brain T-Type Calcium Channels", vol. 276, pp. 3999-4011, 2001, J. of Biological Chemistry.
U. Klockner et al., "Comparison of the CA2+ Currents Induced by Expression of Three Cloned Alpha1 Subunits, Alpha1G, Alpha1H and Alpha11, of Low-Voltage-Activated T-Type Ca2+ Channels", vol. 11, pp. 4171-4178, 1999, E. J. of Neurosciences.
E. Perez-Reyes et al., "Three for T: Molecular Analysis of the Low Voltage-Activated Calcium Channel Family", vol. 56, pp. 660-669, 1999, CMLS.
J. R. Huguenard et al., "Intrathalamic Rhythmicity Studied in vitro: Nominal T-Current Modulation Causes Robust Antioscillatory Effects", vol. 14, pp. 5485-5502, 1994, J. of Neuroscience.

(Continued)

*Primary Examiner* — Shawquia Young
(74) *Attorney, Agent, or Firm* — Sylvia A. Ayler; Gerard M. Devlin

(57) ABSTRACT

A series of N-substituted oxindole derivatives represented by Formula I, or pharmaceutically acceptable salts thereof. Pharmaceutical compositions comprise an effective amount of the instant compounds, either alone, or in combination with one or more other therapeutically active compounds, and a pharmaceutically acceptable carrier. Methods of treating conditions associated with, or caused by, calcium channel activity, including, for example, acute pain, chronic pain, visceral pain, inflammatory pain, neuropathic pain, urinary incontinence, itchiness, allergic dermatitis, epilepsy, diabetic neuropathy, irritable bowel syndrome, depression, anxiety, multiple sclerosis, sleep disorder, bipolar disorder and stroke, comprise administering an effective amount of the present compounds, either alone, or in combination with one or more other therapeutically active compounds.

15 Claims, No Drawings

OTHER PUBLICATIONS

S. J. L. Flatters et al., "T-Type Calcium Channels: A potential Target for the Treatment of Chronic Pain", vol. 30, pp. 573-580, 2005, Drugs of the Future.

E. Bourinet et al, "Silencing of the Cav3.2 T-Type Calcium Channel Gene in Sensory Neurons Demonstrates its major Role in Nociception", vol. 24, pp. 315-324, 2005, EMBO Journal.

J. G. McGivern et al., "Targeting N-type and T-type Calcium Channels for the Treatment of Pain", 2006, vol. 11, pp. 245-253, Drug Discovery Today.

A. Fensome et al., "New Progesterone Receptor Antagonists: 3,3-Disubstituted-5 Aryloxindoles", 2002, vol. 12, pp. 3487-3490, Biorganic & Medicinal Chemistry Letters.

A. Andreani et al., "Cytotoxic Agents from Indole Derivatives and Their Intermediates", 1990, vol. 6, pp. 407-414, Acta Pharm. Nord. 2.

M. Xia et al., "Generation and Characterization of a Cell Line with Inducible Expression of Cav3.2 (T-Type) Channels", vol. 1, pp. 637-645, 2003, Assay and Drug Development Technologies. vol. 3.

J. Lee et al., "Cloning and Expression of Novel Member of the Low Voltage-Activated T-Type Calcium Channel Family", 1999, vol. 19, pp. 1912-1921, J. of Neuroscience.

A. S. Kende et al., "Regioselective C-3 Alkylations of Oxindole Dianion", 1982, vol. 12, pp. 1-10, Synthetic Communications.

S. P. Stanforth et al., "Catalytic Cross-Coupling Reactions in Biaryl Synthesis", 1998, vol. 54, pp. 263-303, Tetrahedron.

O.P. Hamill et al., "Improved Patch-Clamp Techniques for High-Resolution Current Recording from Cells and Cell-Free Membrane Patches",1981, vol. 391, pp. 85-100, Pflugers Archiv E. J. of Physiology.

L. Kiss et al., "High Throughput Ion-Channel Pharmacology: Planar-Array-Based Voltage Clamp", 2003, vol., pp. 127-136, Assay and Drug Development Technologies.

X. Huang et al., "A General and Efficient Copper Catalyst for the Amidation of Aryl Halides", 2002, vol. 124, pp. 7421-7428, J. Am. Chem. Soc.

\* cited by examiner

N-SUBSTITUTED OXINDOLINE DERIVATIVES AS CALCIUM CHANNEL BLOCKERS

CROSS REFERENCE TO RELATED APPLICATIONS

This application is the National Stage of International Application No. PCT/US2008/011290 filed on Sep. 30, 2008, which claims the benefit under 35 U.S.C. 119(e) of U.S. Provisional Applications No. 60/997,624 filed Oct. 4, 2007.

FIELD OF THE INVENTION

This invention relates to a series of N-substituted oxindoline derivatives. In particular, this invention relates to N-substituted oxindoline derivatives that are N-type voltage-gated calcium channel blockers useful for the treatment of a variety of pain conditions including chronic and neuropathic pain. The compounds of the present invention also display activity in connection with block of T-type voltage-gated calcium channels. The compounds described in this invention are useful for the treatment of chronic and acute pain, including neuropathic, inflammatory, and visceral pain. The compounds described in this invention are also useful for the treatment of conditions including disorders of bladder function, pruritis, itchiness, allergic dermatitis and disorders of the central nervous system (CNS) such as stroke, epilepsy, essential tremor, schizophrenia, Parkinson's disease, manic depression, bipolar disorder, depression, anxiety, sleep disorder, diabetic neuropathy, hypertension, cancer, diabetes, infertility and sexual dysfunction.

BACKGROUND TO THE INVENTION

Ion channels control a wide range of cellular activities in both excitable and non-excitable cells (Hille, 2002). Ion channels are attractive therapeutic targets due to their involvement in many physiological processes. In excitable cells, the coordinated function of the resident set of ion channels controls the electrical behavior of the cell. Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-gated calcium channels. Voltage-gated calcium channels provide an important link between electrical activity at the plasma membrane and cell activities that are dependent on intracellular calcium, including muscle contraction, neurotransmitter release, hormone secretion and gene expression. Voltage-gated calcium channels serve to integrate and transduce plasma membrane electrical activity into changes in intracellular calcium concentration, and can do this on a rapid time scale.

Multiple types of calcium channels have been identified in mammalian cells from various tissues, including skeletal muscle, cardiac muscle, lung, smooth muscle and brain. A major family of this type is the L-type calcium channels, which include $Ca_v1.1$, $Ca_v1.2$, $Ca_v1.3$, and $Ca_v1.4$, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T ($Ca_v3.1$ and $Ca_v3.2$), N ($Ca_v2.2$), P/Q ($Ca_v2.1$) and R ($Ca_v2.3$). The "T-type" (or "low voltage-activated") calcium channels are so named because they open for a shorter duration (T=transient) than the longer (L=long-lasting) openings of the L-type calcium channels. The L, N, P and Q-type channels activate at more positive potentials (high voltage activated) and display diverse kinetics and voltage-dependent properties.

Because of the crucial role in cell physiology, modulation of calcium channel activity can have profound effects. Mutations in calcium channel subunits have been implicated in a number of genetic diseases including familial hemiplegic migraine, spinocerebellar ataxia, Timothy Syndrome, incomplete congenital stationary night blindness and familial hypokalemic periodic paralysis. Modulation of voltage-gated calcium channels by signaling pathways, including c-AMP-dependent protein kinases and G proteins is an important component of signaling by hormones and neurotransmitters (Catterall, 2000). Pharmacological modulation of calcium channels can have significant therapeutic effects, including the use of L-type calcium channel ($Ca_v1.2$) blockers in the treatment of hypertension (Hockerman, et al., 1997) and more recently, use of Ziconotide, a peptide blocker of N-type calcium channels ($Ca_v2.2$), for the treatment of intractable pain (Staats, et al., 2004). Zicontide is derived from Conotoxin, a peptide toxin isolated from cone snail venom, must be applied by intrathecal injection to allow its access to a site of action in the spinal cord and to minimize exposure to channels in the autonomic nervous system that are involved in regulating cardiovascular function. Ziconotide has also been shown to highly effective as a neuroprotective agent in rat models of global and focal ischemia (Colburne et. Al., Stroke (1999) 30, 662-668) suggesting that modulation of N-type calcium channels ($Ca_v2.2$) has implication in the treatment of stroke.

Clinical and preclinical experiments with ziconotide and related peptides confirm a key role of N-type calcium channels in transmitting nociceptive signals into the spinal cord. Identification of N-type calcium channel blockers that can be administered systemically, and effectively block N-type calcium channels in the nociceptive signaling pathway, while sparing N-type calcium channel function in the periphery would provide important new tools for treating some forms of pain. The present invention describes blockers of N-type calcium channels ($Ca_v2.2$) that display functional selectivity by blocking N-type calcium channel activity needed to maintain pathological nociceptive signaling, while exhibiting a lesser potency at blocking N-type calcium channels involved in maintaining normal cardiovascular function. See WO2007085357, and WO2007028638.

There are three subtypes of T-type calcium channels that have been identified from various warm blooded animals including rat [J. Biol. Chem. 276(6) 3999-4011 (2001); Eur J Neurosci 11(12):4171-8 (1999); reviewed in Cell Mol Life Sci 56(7-8):660-9 (1999)]. These subtypes are termed α1G, α1H, and α1I, and the molecular properties of these channels demonstrate 60-70% homology in the amino acid sequences. The electrophysiological characterization of these individual subtypes has revealed differences in their voltage-dependent activation, inactivation, deactivation and steady-state inactivation levels and their selectivity to various ions such as barium (J Biol. Chem. 276(6) 3999-4011 (2001)). Pharmacologically, these subtypes have shown differing sensitivities to blockade by ionic nickel. These channel subtypes are also expressed in various forms due to their ability to undergo various splicing events during their assembly (J Biol. Chem. 276 (6) 3999-4011 (2001)).

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophrenia, cardiac arrhythmia, hypertension, pain, cancer, diabetes, infertility and sexual dysfunction (J Neuroscience, 14, 5485 (1994); Drugs Future 30(6), 573-580 (2005); EMBO J, 24, 315-324 (2005); Drug Discovery Today, 11, 5/6, 245-253 (2006)). See also patent and publications US2007/0105820, U.S. Pat. No. 6,462,032, U.S. Pat. No. 7,084,168, U.S. Pat. No. 6,608,068, U.S. Pat. No. 7,253,203, WO86/03749, WO91/06545, WO91/04974, US2006/0258659, US2006/0252812, US2006/0252758, Fensome et al., Bioorg. Med. Chem. Lett. 12, 3487-3490 (2002), and Andreani et al, Acta Pharm Nord., 2(6), 407-414 (1990). See also simultaneously filed application referred to as Ser. No. 60/997,705, herein incorporated by reference in its entirety.

SUMMARY OF THE INVENTION

The present invention is directed to a series of N-substituted oxindoline derivatives that are N-type calcium channel (Cav2.2) blockers useful for the treatment of acute pain, chronic pain, cancer pain, visceral pain, inflammatory pain, neuropathic pain, post-herpetic neuralgia, diabatic neuropathy, trigeminal neuralgia, migraine, fibromyalgia and stroke. The compounds of the present invention also display activities on T-type voltage-activated calcium channels (Cav 3.1 and Cav 3.2). The compounds described in this invention are also useful for the treatment of other conditions, including disorders of bladder function, pruritis, itchiness, allergic dermatitis and disorders of the central nervous system (CNS) such as stroke, epilepsy, essential tremor, schizophrenia, Parkinson's disease, manic depression, bipolar disorder, depression, anxiety, sleep disorder, hypertension, cancer, diabetes, infertility and sexual dysfunction. This invention also provides pharmaceutical compositions comprising a compound of the present invention, either alone, or in combination with one or more therapeutically active compounds, and a pharmaceutically acceptable carrier.

This invention further comprises methods for the treatment of acute pain, chronic pain, visceral pain, inflammatory pain, neuropathic pain and disorders of the CNS including, but not limited to, epilepsy, manic depression, depression, anxiety and bipolar disorder comprising administering the compounds and pharmaceutical compositions of the present invention. This invention further comprises use of compounds of formula I in the manufacture of a medicament for treating acute pain, chronic pain, visceral pain, inflammatory pain, neuropathic pain and disorders of the CNS including, but not limited to, epilepsy, manic depression, depression, anxiety and bipolar disorder.

DETAILED DESCRIPTION OF THE INVENTION

The compounds of this invention are represented by Formula I:

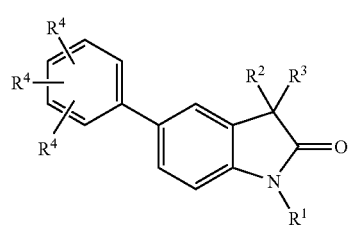

or pharmaceutically acceptable salts thereof and individual enantiomers and diastereomers thereof: wherein:

$R^1$=aryl or heteroaryl, optionally substituted with 1-3 substituents consisting of: $C_{1-6}$ alkyl, $C_1$-$C_4$-fluoroalkyl, $C_{6-10}$-aryl, or $C_{6-10}$heteroaryl, F, Cl, Br, CN, $OR^5$, $NR^5R^6$, $SO_2R^5$, $SO_2NR^5R^6$, $NR^5SO_2R^6$, $CO_2R^5$, $CONR^5R^6$;

$R^2$=$C_{1-6}$ alkyl, $C_{1-6}$ fluoroalkyl;

$R^3$=$(CH_2)_n$aryl or $(CH_2)_n$heteroaryl, wherein each aryl or heteroaryl is optionally substituted with 1-3 substituents consisting of: $C_{1-6}$ alkyl, $C_{1-4}$-fluoroalkyl, $C_{6-10}$-aryl, or $C_{6-10}$heteroaryl, F, Cl, Br, CN, $OR^5$, $NR^5R^6$, $SO_2R^5$, $SO_2NR^5R^6$, $NR^5SO_2R^6$, $CO_2R^5$, $CONR^5R^6$;

each $R^4$ is independently selected from H, $C_{1-6}$ alkyl, $C_{1-4}$-fluoroalkyl, aryl or heteroaryl, F, Cl, Br, CN, $OR^5$, $NR^5R^6$, $SO_2R^5$, $SO_2NR^5R^6$, $NR^5SO_2R^6$, $CO_2R^5$, $CONR^5R^6$;

$R^5$ and $R^6$ are each independently selected from H, $C_{1-6}$ alkyl, $C_{1-4}$-fluoroalkyl, $C_{3-7}$-cycloalkyl, $C_{6-10}$-aryl, and $C_{6-10}$heteroaryl or $R^5$ and $R^6$ join to form a 3-7 member carbocyclic or heterocyclic ring and n=0-6.

In a preferred embodiment of the compounds of the present invention, $R^2$ is methyl, as represented by formula Ia.

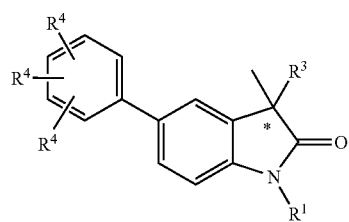

and all other variables are as described herein. A sub-embodiment of formula Ia is realized when $R^3$ is a methylene-linked aryl or heteroaryl substituent.

Another embodiment of this invention is realized when the stereocenter depicted by "*" in formula I is in the S or R stereochemical configuration, preferably the R configuration and all other variables are as originally described.

Still another embodiment of this invention is realized when $R^1$ in structural formula I is an aryl, optionally substituted and all other variables are as originally described.

Yet another embodiment of this invention is realized when $R^1$ is structural formula I is a heteroaryl, optionally substituted and all other variables are as originally described.

Another embodiment of this invention is realized by structural formula Ib

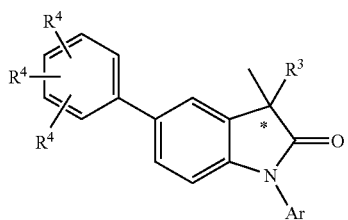

Wherein Ar is an aryl optionally substituted and all other variables are as originally described. A sub-embodiment of formula Ib is realized when $R^3$ is a methylene-linked aryl or heteroaryl substituent and the stereocenter depicted by "*" in formula Ib is in the R stereochemical configuration. Still another sub-embodiment of formula Ib is realized when Ar is selected from the group consisting of phenyl, napthyl, tetrahydronapthyl, indanyl, and biphenyl, preferably phenyl. Yet another sub-embodiment of formula Ic is realized when $R^3$ is selected from the group consisting of phenyl, napthyl, tetrahydronapthyl, indanyl, and biphenyl, furyl, imidazolidinyl, imidazolinyl, imidazolyl, indolinyl, indolyl, isoquinolinyl, morpholinyl, oxazolyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, and quinolinyl, preferably pyrimidinyl or phenyl.

Another embodiment of this invention is realized by structural formula Ic

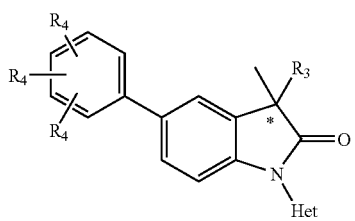

Wherein Het is a heteroaryl optionally substituted and all other variables are as originally described. A sub-embodiment of formula Ic is realized when $R^3$ is a methylene-linked aryl or heteroaryl substituent and the stereocenter depicted by "*" in formula Ic is in the R stereochemical configuration. Still another sub-embodiment of formula Ic is realized when Het is selected from the group consisting of thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, triazolyl, oxazolyl, thiazolyl, and isoxazoyl, preferably tetrazolyl, triazolyl, pyrimidinyl, or pyridyl. Yet another sub-embodiment of formula Ic is realized when $R^3$ is selected from the group consisting of phenyl, napthyl, tetrahydronapthyl, indanyl, and biphenyl, furyl, imidazolidinyl, imidazolinyl, imidazolyl, indolinyl, indolyl, isoquinolinyl, morpholinyl, oxazolyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, and quinolinyl, preferably pyrimidinyl or phenyl.

Another embodiment of this invention is realized when $R^1$ and $R^3$ both are $(CH_2)_n$heteroaryl and all other variables are as described herein. A sub-embodiment of this invention is realized when n for $R^1$ is zero and for $R^3$ is 1. Another sub-embodiment of this invention is realized when $R^1$ is selected from the group consisting of tetrazolyl, triazolyl, pyrimidinyl, and pyridyl and $R^3$ is selected from the group consisting of pyrimidinyl or phenyl. Still another sub-embodiment of this invention is realized when the stereocenter depicted by "*" is in the R stereochemical configuration.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" as well as other groups having the prefix "alk" such as, for example, alkoxy, alkanoyl, alkenyl, and alkynyl means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl," "alkynyl" and other like terms include carbon chains containing at least one unsaturated C—C bond.

As used herein, "fluoroalkyl" refers to an alkyl substituent as described herein containing at least one flurine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, triazolyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperidinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl tetrazolyl, and triazolyl.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S. Preferred heteroaryl groups include, without limitation, thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, triazolyl, oxazolyl, thiazolyl, and isoxazolyl.

In certain other preferred embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrrolidinyl, piperidinyl, piperazinyl, morpholinyl, tetrahydrofuranyl, imidazolinyl, pyrrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2,4-fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" refers to fluorine, chlorine, bromine and iodine.

The term "mammal" "mammalian" or "mammals" includes humans, as well as animals, such as dogs, cats, horses, pigs and cattle.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin, and xvi) sodium channel blockers. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, small fiber neuropathy, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohn's disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

In addition to primates, such as humans, a variety of other mammals can be treated according to the method of the present invention. For instance, mammals including, but not limited to, cows, sheep, goats, horses, dogs, cats guinea pigs, or other bovine, ovine, equine, canine, feline, rodent such as mouse, species can be treated. However, the method can also be practiced in other species, such as avian species (e.g., chickens).

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-HT}_{1A}$ agonists or antagonists, especially $5\text{-HT}_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with calcium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are advantageous oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet advantageously contains from about 0.1 mg to about 500 mg of the active ingredient and each cachet or capsule advantageously containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The compounds and pharmaceutical compositions of this invention have been found to block N-type, T-type, and L-type calcium channels. Accordingly, an aspect of the invention is the treatment and prevention in mammals of conditions that are amenable to amelioration through blockage of said calcium channels by administering an effective amount of a compound of this invention. Such conditions include, for example, acute pain, chronic pain, visceral pain, inflammatory pain and neuropathic pain. These conditions may also include epilepsy, essential tremor, schizophrenia, Parkinson's disease, depression, anxiety, sleep disorders, sleep disturbances, psychosis, infertility, and sexual dysfunction. These conditions may further include cardiac arrhythmia and hypertension. The instant compounds and compositions are useful for treating and preventing the above-recited conditions, in humans and non-human mammals such as dogs and cats. It is understood that the treatment of mammals other than humans refers to the treatment of clinical conditions in non-human mammals that correlate to the above-recited conditions.

Further, as described above, the instant compounds can be utilized in combination with one or more therapeutically active compounds. In particular, the inventive compounds can be advantageously used in combination with i) opiate agonists or antagonists, ii) other calcium channel antagonists, iii) 5HT receptor agonists or antagonists, including 5-HT$_{1A}$ agonists or antagonists, and 5-HT$_{1A}$ partial agonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, xiv) norepinephrine reuptake inhibitors, xv) monoamine oxidase inhibitors (MAOIs), xvi) reversible inhibitors of monoamine oxidase (RIMAs), xvii) alpha-adrenoreceptor antagonists, xviii) atypical anti-depressants, xix) benzodiazepines, xx) corticotropin releasing factor (CRF) antagonists, xxi) neurontin (gabapentin) xxii) pregabalin and xxiii) sodium channel blockers.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, CAMP (cyclic adenosine-3',5'-monophosphate), DAST ((diethylamino)sulfur trifluoride), DBU (1,8-diazabicyclo[5.4.0]undec-7-ene), DIBAL (diisobutylaluminum hydride), DIEA (diisopropylethyl amine), DMAP (4-(dimethylamino)pyridine), DMF (N,N-dimethylformamide), DPPF (1,1'-bisdiphenylphosphino ferrocene), EDC (1-(3-dimethylaminopropyl)-3-ethylcarbodiimide hydrochloride), Et$_3$N (triethylamine), GST (glutathione transferase), HOBt (1-hydroxybenzotriazole), LAH (lithium aluminum hydride), Ms (methanesulfonyl; mesyl; or SO$_2$Me), MsO (methanesulfonate or mesylate), MCPBA (meta-chloro perbenzoic acid), NaHMDS (sodium hexamethyldisilazane), NBS (N-bromosuccinimide), NCS(N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or SO$_2$NH$_2$), SPA (scintillation proximity assay), Th (2- or 3-thienyl), TFA (trifluoroacetic acid), THF (Tetrahydrofuran), Thi (Thiophenediyl), TLC (thin layer chromatography), TMEDA (N,N,N',N'-tetramethylethylenediamine), TMSI (trimethylsilyl iodide), Tr or trityl (N-triphenylmethyl), C$_3$H$_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the general Schemes provided below as well as the procedures provided in the Examples. The following Schemes and Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

ASSAY EXAMPLE 1

Fluorescent Assay for Cav2.2 Channels Using Potassium Depolarization to Initiate Channel Opening Human Cav2.2 channels were stably expressed in HEK293 cells along with alpha2-delta and beta subunits of voltage-gated calcium channels. An inwardly rectifying potassium channel (Kir2.3) was also expressed in these cells to allow more precise control of the cell membrane potential by extracellular potassium concentration. At low bath potassium concentration, the membrane potential is relatively negative, and is depolarized as the bath potassium concentration is raised. In this way, the bath potassium concentration can be used to regulate the voltage-dependent conformations of the channels. Compounds are incubated with cells in the presence of low (4 mM) potassium or elevated (12, 25 or 30 mM) potassium to determine the affinity for compound block of resting (closed) channels at 4 mM potassium or affinity for block of open and inactivated channels at 12, 25 or 30 mM potassium. After the incubation period, Cav2.2 channel opening is triggered by addition of higher concentration of potassium (70 mM final concentration) to further depolarize the cell. The degree of state-dependent block can be estimated from the inhibitory potency of compounds after incubation in different potassium concentrations.

Calcium influx through Cav2.2 channels is determined using a calcium-sensitive fluorescent dye in combination with a fluorescent plate reader. Fluorescent changes were measured with either a VIPR (Aurora Instruments) or FLIPR (Molecular Devices) plate reader.

Protocol
1. Seed cells in Poly-D-Lysine Coated 96- or 384-well plate and keep in a 37° C.-10% CO$_2$ incubator overnight
2. Remove media[1], wash cells with 0.2 mL (96-well plate) or 0.05 mL (384-well plate) Dulbecco's Phosphate Buffered Saline (D-PBS) with calcium & magnesium (Invitrogen; 14040)
3. Add 0.1 mL (96-well plate) or 0.05 mL (384-well plate) of 4 μM fluo-4 (Molecular Probes; F-14202) and 0.02% Pluronic acid (Molecular Probes; P-3000) prepared in D-PBS with calcium & magnesium (Invitrogen; 14040) supplemented with 10 mM Glucose & 10 mM Hepes/NaOH; pH 7.4
4. Incubate in the dark at 25° C. for 60-70 min
5. Remove dye[2], wash cells with 0.1 mL (96-well plate) or 0.06 mL (384-well plate) of 4, 12, 25, or 30 mM Potassium Pre-polarization Buffer. (PPB)
6. Add 0.1 mL (96-well plate) or 0.03 mL (384-well plate) of 4, 12, 25, 30 mM PPB. with or without test compound
7. Incubate in the dark at 25° C. for 30 min
8. Read cell plate on VIPR instrument, Excitation=480 nm, Emission=535 nm
9. With VIPR continuously reading, add 0.1 mL (96-well plate) or 0.03 mL (384-well plate) of Depolarization Buffer, which is 2× the final assay concentration, to the cell plate.

Assay Reagents:

| 4 mM K Pre-Polarization Buffer | 12 mM K Pre-Polarization Buffer | 25 mM K Pre-Polarization Buffer | 30 mM K Pre-Polarization Buffer | 140 mM K Depolarization Buffer |
|---|---|---|---|---|
| 146 mM NaCl | 138 mM NaCl | 125 mM NaCl | 120 mM NaCl | 10 mM NaCl |
| 4 mM KCl | 12 mM KCl | 25 mM KCl | 30 mM KCl | 140 mM KCl |
| 0.8 mM CaCl$_2$ | 0.8 mM CaCl$_2$ | 0.8 mM CaCl$_2$ | 0.8 mM CaCl$_2$ | 0.8 mM CaCl$_2$ |
| 1.7 mM MgCl$_2$ | 1.7 mM MgCl$_2$ | 1.7 mM MgCl$_2$ | 1.7 mM MgCl$_2$ | 1.7 mM MgCl$_2$ |
| 10 mM HEPES | 10 mM HEPES | 10 mM HEPES | 10 mM HEPES | 10 mM HEPES |
| pH = 7.2 | pH = 7.2 | pH = 7.2 | pH = 7.2 | pH = 7.2 |

ASSAY EXAMPLE 2

Electrophysiological Measurement of Block of Cav2.2 Channels Using Automated Electrophysiology Instruments Block of N-type calcium channels is evaluated utilizing the IonWorks HT 384 well automated patch clamp electrophysiology device. This instrument allows synchronous recording from 384 wells (48 at a time). A single whole cell recording is made in each well. Whole cell recording is established by perfusion of the internal compartment with amphotericin B.

The voltage protocol is designed to detect use-dependent block. A 2 Hz train of depolarizations (twenty 25 ms steps to +20 mV). The experimental sequence consists of a control train (pre-compound), incubation of cells with compound for 5 minutes, followed by a second train (post-compound). Use dependent block by compounds is estimated by comparing fractional block of the first pulse in the train to block of the 20th pulse.

Protocol

Parallel patch clamp electrophysiology is performed using IonWorks HT (Molecular Devices Corp.) essentially as described by Kiss and colleagues [Kiss et al. 2003; Assay and Drug Development Technologies, 1:127-135]. Briefly, a stable HEK 293 cell line (referred to as CBK) expressing the N-type calcium channel subunits (alpha$_{1B}$, alpha$_2$-delta, beta$_{3a}$,) and an inwardly rectifying potassium channel (K$_{ir}$-2.3) is used to record barium current through the N-type calcium channel. Cells are grown in T75 culture plates to 60-90% confluence before use. Cells are rinsed 3× with 10 mL PBS (Ca/Mg-free) followed by addition of 1.0 mL 1× trypsin to the flask. Cells are incubated at 37° C. until rounded and free from plate (usually 1-3 min). Cells are then transferred to a 15 mL conical tube with 13 mL of CBK media containing serum and antibiotics and spun at setting 2 on a table top centrifuge for 2 min. The supernatant is poured off and the pellet of cells is resuspended in external solution (in mM): 120 NaCl, 20 $BaCl_2$, 4.5 KCl, 0.5 $MgCl_2$, 10 HEPES, 10 Glucose, pH=7.4). The concentration of cells in suspension is adjusted to achieve 1000-3000 cells per well. Cells are used immediately once they have been resuspended. The internal solution is (in mM): 100 K-Gluconate, 40 KCl, 3.2 $MgCl_2$, 3 EGTA, 5 HEPES, pH 7.3 with KOH. Perforated patch whole cell recording is achieved by added the perforating agent amphotericin B to the internal solution. A 36 mg/mL stock of amphtericn B is made fresh in dimethyl sulfoxide for each run. 166 μl of this stock is added to 50 mL of internal solution yielding a final working solution of 120 ug/mL.

Voltage protocols and the recording of membrane currents are performed using the IonWorks HT software/hardware system. Currents are sampled at 1.25 kHz and leakage subtraction is performed using a 10 mV step from the holding potential and assuming a linear leak conductance. No correction for liquid junction potentials is employed. Cells are voltage clamped at −70 mV for 10 s followed by a 20 pulse train of 25 ms steps to +20 mV at 2 Hz. After a control train, the cells are incubated with compound for 5 minutes and a second train is applied. Use dependent block by compounds is estimated by comparing fractional block of the first pulse to block of the 20th pulse. Wells with seal resistances less than 70 MOhms or less than 0.1 nA of Ba current at the test potential (+20 mV) are excluded from analysis. Current amplitudes are calculated with the IonWorks software. Relative current, percent inhibition and IC50s are calculated with a custom Excel/Sigmaplot macro.

Compounds are added to cells with a fluidics head from a 96-well compound plate. To compensate for the dilution of compound during addition, the compound plate concentration is 3× higher than the final concentration on the patch plate.

Two types of experiments are generally performed: screens and titrations. In the screening mode, 10-20 compounds are evaluated at a single concentration (usually 3 uM). The percent inhibition is calculated from the ratio of the current amplitude in the presence and absence of compound, normalized to the ratio in vehicle control wells. For generation of IC50s, a 10-point titration is performed on 2-4 compounds per patch plate. The range of concentrations tested is generally 0.001 to 20 uM. IC50s are calculated from the fits of the Hill equation to the data. The form of the Hill equation used is: Relative Current=Max Min)/(1+(conc/IC50)^slope))+ Min. Vehicle controls (dimethyl sulfoxide) and 0.3 mM $CdCl_2$ (which inhibits the channel completely) are run on each plate for normalization purposes and to define the Max and Min.

ASSAY EXAMPLE 3

Electrophysiological Measurement of Block of Cav2.2 Channels Using Whole Cell Voltage Clamp and Using PatchXpress Automated Electrophysiology Instrument Block of N-type calcium channels is evaluated utilizing manual and automated (PatchXpress) patch clamp electrophysiology. Voltage protocols are designed to detect state-dependent block. Pulses (50 ms) are applied at a slow frequency (0.067 Hz) from polarized (−90 mV) or depolarized (−40 mV) holding potentials. Compounds which preferentially block inactivated/open channels over resting channels will have higher potency at −40 mV compared to −90 mV.

Protocol:

A stable HEK 293 cell line (referred to as CBK) expressing the N-type calcium channel subunits ($alpha_{1B}$, $alpha_2$-delta, $beta_{3a}$,) and an inwardly rectifying potassium channel ($K_{ir}2.3$) is used to record barium current through the N-type calcium channel. Cells are grown either on poly-D-lysine coated coverglass (manual EP) or in T75 culture plates (PatchXpress). For the PatchXpress, cells are released from the flask using tryspin. In both cases, the external solution is (in mM): 120 NaCl, 20 $BaCl_2$, 4.5 KCl, 0.5 $MgCl_2$, 10 HEPES, 10 Glucose, pH 7.4 with NaOH. The internal solution is (in mM): 130 CsCl, 10 EGTA, 10 HEPES, 2 $MgCl_2$, 3 MgATP, pH 7.3 with CsOH.

Barium currents are measured by manual whole-cell patch clamp using standard techniques (Hamill et. al. Pfluegers Archiv 391:85-100 (1981)). Microelectrodes are fabricated from borosilicate glass and fire-polished. Electrode resistances are generally 2 to 4 MOhm when filled with the standard internal saline. The reference electrode is a silver-silver chloride pellet. Voltages are not corrected for the liquid junction potential between the internal and external solutions and leak is subtracted using the P/n procedure. Solutions are applied to cells by bath perfusion via gravity. The experimental chamber volume is ~0.2 mL and the perfusion rate is 0.5-2 mL/min. Flow of solution through the chamber is maintained at all times. Measurement of current amplitudes is performed with PULSEFIT software (HEKA Elektronik).

PatchXpress (Molecular Devices) is a 16-well whole-cell automated patch clamp device that operates asynchronously with fully integrated fluidics. High resistance (gigaohm) seals are achieved with 50-80% success. Capacitance and series resistance compensation is automated. No correction for liquid junction potentials is employed. Leak is subtracted using the P/n procedure. Compounds are added to cells with a pipettor from a 96-well compound plate. Voltage protocols and the recording of membrane currents are performed using the PatchXpress software/hardware system. Current amplitudes are calculated with DataXpress software.

In both manual and automated patch clamp, cells are voltage clamped at −40 mV or −90 mV and 50 ms pulses to +20 mV are applied every 15 sec (0.067 Hz). Compounds are added in escalating doses to measure % Inhibition. Percent inhibition is calculated from the ratio of the current amplitude in the presence and absence of compound. When multiple doses are achieved per cell, IC50s are calculated. The range of concentrations tested is generally 0.1 to 30 uM. IC50s are calculated from the fits of the Hill equation to the data. The form of the Hill equation used is: Relative Current=1/(1+(conc/IC50)^slope)).

The intrinsic N-type calcium channel antagonist activity of a compound which may be used in the present invention may be determined by these assays.

In particular, the compounds of the following examples had activity in antagonizing the N-type calcium channel in the aforementioned assays, generally with an IC50 of less than about 10 uM. Preferred compounds within the present invention had activity in antagonizing the N-type calcium channel in the aforementioned assays with an $IC_{50}$ of less than about 1 uM. By way of example, the compounds of examples 2, 10 and 18 have IC50s of 0.23 uM, 0.52 uM, and 0.26 uM respectively. Such a result is indicative of the intrinsic activity of the compounds in use as antagonists of N-type calcium channel activity.

ASSAY EXAMPLE 4

Assay for Cav1 and Cav3.2 Channels

The T-type calcium channel blocking activity of the compounds of this invention may be readily determined using the methodology well known in the art described by Xia, et al., Assay and Drug Development Tech., 1(5), 637-645 (2003).

In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. No. 5,618,720, U.S. Pat. No. 5,686,241, U.S. Pat. No. 5,710,250, U.S. Pat. No. 5,726,035, U.S. Pat. No. 5,792,846, U.S. Pat. No. 5,846,757, U.S. Pat. No. 5,851,824, U.S. Pat. No. 5,874,236, U.S. Pat. No. 5,876,958, U.S. Pat. No. 6,013,474, U.S. Pat. No. 6,057,114, U.S. Pat. No. 6,096,514, WO 99/28342, and J. Neuroscience, 19(6):1912-1921 (1999). Cells expressing the t-type channels were grown in H3D5 growth media which comprised DMEM, 6% bovine calf serum (HYCLONE), 30 micromolar Verapamil, 200 microgram/mL Hygromycin B, 1× Penicillin/Streptomycin. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05 Trypsin, 0.53 mM EDTA. The extracellular recording solution consists of (mM): 130 mM NaCl, 4 mM KCl, 1 mM $MgCl_2$, 2 mM $CaCl_2$, 10 mM HEPES, 30 Glucose, pH 7.4. The internal solution consists of (mM): 135 mM CsMeSO4, 1 $MgCl_2$, 10 CsCl, 5 EGTA, 10 HEPES, pH 7.4, or 135 mM CsCl, 2 $MgCl_2$, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) −80 mV holding potential every 20 seconds pulse to −20 mV for 40 msec duration; the effectiveness of the drug in inhibiting the current mediated by the channel is measured directly from measuring the reduction in peak current amplitude initiated by the voltage shift from −80 mV to −20 mV; (2). −100 mV holding potential every 15 seconds pulse to −20 mV for 40 msec duration; the effectiveness of the drug in inhibiting the current mediated by the channel is measured directly from measuring the reduction in peak current amplitude initiated by the shift in potential from −100 mV to −30 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays.

In particular, the compounds of the following examples had activity in antagonizing the T-type calcium channel in the aforementioned assays, generally with an $IC_{50}$ of less than about 10 uM. Preferred compounds within the present invention had activity in antagonizing the T-type calcium channel in the aforementioned assays with an $IC_{50}$ of less than about 1 uM. Such a result is indicative of the intrinsic activity of the compounds in use as antagonists of T-type calcium channel activity.

In Vivo Assay: (Rodent CFA Model):

Male Sprague Dawley rats (300-400 gm) were administered 200 microl CFA (Complete Freund's Adjuvant) three days prior to the study. CFA is *mycobacterium tuberculosis* suspended in saline (1:1; Sigma) to form an emulsion that contains 0.5 mg mycobacterium/mL. The CFA was injected into the plantar area of the left hind paw.

Rats are fasted the night before the study only for oral administration of compounds. On the morning of test day using a Ugo Basile apparatus, 2 baseline samples are taken 1 hour apart. The rat is wrapped in a towel. Its paw is placed over a ball bearing and under the pressure device. A foot pedal is depressed to apply constant linear pressure. Pressure is stopped when the rat withdraws its paw, vocalizes, or struggles. The right paw is then tested. Rats are then dosed with compound and tested at predetermined time points. Compounds were prepared in dimethyl sulfoxide (15%)/PEG300 (60%)/Water (25%) and were dosed in a volume of 2 mL/kg.

Percent maximal possible effect (% MPE) was calculated as: (post-treatment−pre-treatment)/(pre-injury threshold−pre-treatment)×100. The % responder is the number of rats that have a MPE. 30% at any time following compound administration. The effect of treatment was determined by one-way ANOVA Repeated Measures Friedman Test with a Dunn's post test.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 5$^{th}$ Ed., John Wiley and Sons, New York, N.Y., 2001; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. Other references used for synthesizing novel compounds in the present invention include: *Synthetic Communications*, Kende and Hodges, 1982, 12 (1), 1-10 and *Journal of the American Chemical Society*, Klapars, Huang and Buchwald, 2002, 124, 7421-7428. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^1$H and $^{13}$C NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyl-lithium, phenyllithium, alkyl magnesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

It is also understood that compounds listed in the Schemes and Tables below that contain one or more stereocenters may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

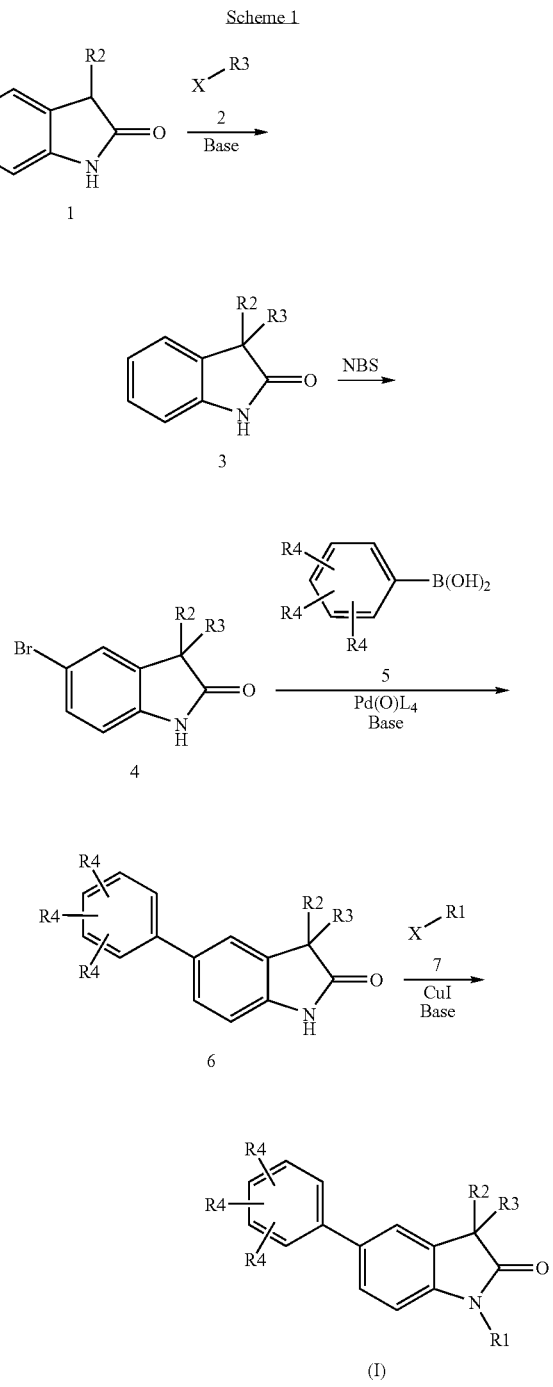

The compounds of the present invention may be prepared as illustrated in Scheme 1. An appropriately substituted oxindole 1 may be commercially available, such as 3-methyloxindole, or may be readily prepared using the references cited above by those skilled in the art. The oxindole may be deprotonated using two equivalents of an appropriate base such as lithium hexamethyldisilazane, lithium diisopropylamide, or a combination of n-butyllithium and tetramethylethylamine diamine, in anaprotic solvent such as tetrahydrofuran, at temperatures ranging from −78° C. to ambient temperature. To this intermediate may be added an appropriately substituted electrophile 2 to afford intermediates such as 3. Electrophiles such as 2 may be commercially available, such as benzyl bromide or appropriately substituted benzyl bromides, or may be readily prepared using the references cited above by those skilled in the art. Treatment of intermediate 3 with a halogenating agent such as N-bromosuccinimide (NBS) in an aprotic solvent such as N,N-dimethylformamide at ambient temperature selectively affords the 5-bromooxindole derivative 4. This intermediate may then be coupled with an appropriately substituted phenylboronate 5 in the presence of a palladium catalyst such as tetrakis(triphenylphosphine)palladium(0), tris(dibenzylideneacetone)dipalladium(0), or [1,1'-bis(diphenylphosphino)ferrocene]dichloropalladium(II), complex with dichloromethane, and an alkaline base such as sodium carbonate, in an appropriate solvent such as toluene, ethanol, or a mixture of solvents, at ambient temperature to 100° C. to afford the coupled biaryl intermediate 6. Alternative aryl coupling methods to prepare derivatives such as 6 from 4 are also available, and will be readily apparent to those skilled in the art, or using the methods reviewed in *Tetrahedron*, Stanforth, 1998, 54, 263-303. Intermediate 6 may be coupled with an appropriately substituted aromatic or heteroaromatic halide 7, in the presence of CuI and a base mixture such as potassium carbonate and N,N-dimethylethyene diamine in a solvent such as toluene at 100° C. to afford compounds of the formula I. Aromatic and heteroaromatic halides 7 may be commercially available, such as 2-bromopyrimidine, or may be readily synthesized by those skilled in the art.

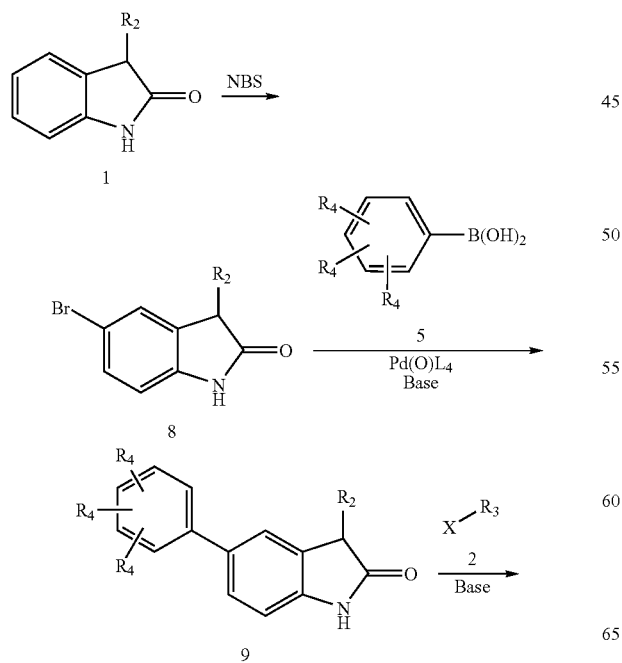

Scheme 2

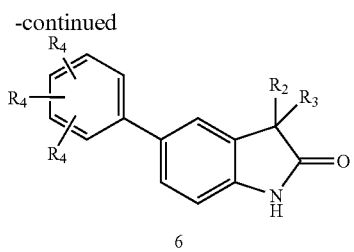
6

The compounds of the present invention may also be prepared as illustrated in Scheme 2. An appropriately substituted oxindole 1 may be commercially available, such as 3-methyloxindole, or may be readily prepared using the references cited above by those skilled in the art. Treatment of the oxindole with a halogenating agent such as N-bromosuccinimide (NBS) in an aprotic solvent such as N,N-dimethylformamide at ambient temperature selectively affords the 5-bromooxindole derivative 8. This intermediate may then be coupled with an appropriately substituted phenylboronate 5 in the presence of a palladium catalyst such as tetrakis(triphenylphosphine)palladium(0), tris(dibenzylideneacetone)dipalladium(0), or [1,1'-bis(diphenylphosphino)ferrocene]dichloropalladium (II), complex with dichloromethane, and an alkaline base such as sodium carbonate, in an appropriate solvent such as toluene, ethanol, or a mixture of solvents, at ambient temperature to 100° C. to afford the coupled biaryl intermediate 9. Alternative aryl coupling methods to prepare derivatives such as 9 from 8 are also available, and will be readily apparent to those skilled in the art, or using the methods reviewed in *Tetrahedron*, Stanforth, 1998, 54, 263-303. Intermediate 9 may be deprotonated using two equivalents of an appropriate base such as lithium hexamethyldisilazane, lithium diisopropylamide, or a combination of n-butyllithium and tetramethylethylamine diamine, in an aprotic solvent such as tetrahydrofuran, at temperatures ranging from −78° C. to ambient temperature. To this intermediate may be added an appropriately substituted electrophile 2 to afford intermediates such as 6. Electrophiles such as 2 may be commercially available, such as benzyl bromide or appropriately substituted benzyl bromides, or may be readily prepared using the references cited above by those skilled in the art. Intermediate 6 may then be further manipulated as described in Scheme 1 to afford compounds of the formula I.

EXAMPLE 1

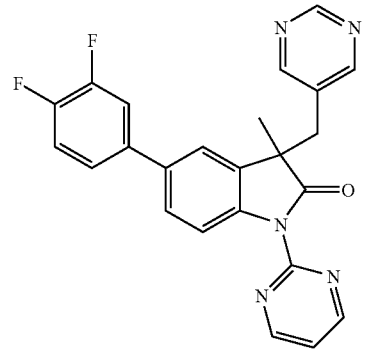

5-(3,4-difluorophenyl)-3-methyl-1-pyrimidin-2-yl-3-(pyrimidin-5-ylmethyl)-1,3-dihydro-2H-indol-2-one Step 1: Preparation of pyrimidin-5-ylmethanol

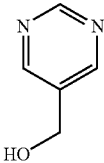

Pyrimidine-5-carboxaldehyde (14.97 g, 138.0 mmol) in methanol (80 mL) at 0° C. was treated portionwise with sodium borohydride (5.24 g, 138 mmol). The resulting mixture was stirred at 0° C. for 1 hour. The mixture was quenched carefully with acetone, then concentrated under reduced pressure. The residue was purified by column chromatography on silica gel Biotage 40M, eluting with 5% methanol/dichloromethane, to give pyrimidin-5-ylmethanol as a white crystalline solid.

$^1$H NMR (CDCl$_3$): δ 9.18 (s, 1H), 8.78 (s, 2H), 4.81 (s, 2H)
MS: m/e 111.04 (M+H)$^+$

Step 2: Preparation of 3-methyl-3-(pyrimidin-5-ylmethyl)-1,3-dihydro-2H-indol-2-one

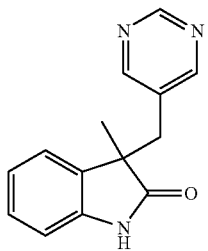

Pyrimidin-5-ylmethanol (510 mg, 4.63 mmol) in tetrahydrofuran (8 mL) at room temperature was treated with sodium hydride (185 mg, 4.63 mmol) and stirred for 5 minutes. p-Toluenesulfonyl chloride (883 mg, 4.63 mmol) was added, and the resulting mixture stirred for one hour to form pyrimidin-5-ylmethyl 4-methylbenzenesulfonate. In a separate flask 3-methyloxindole (682 mg, 4.63 mmol) and N,N'-dimethylethylenediamine (1.538 mL, 10.19 mmol) in tetrahydrofuran (16 mL) were cooled to −78° C. and treated dropwise with n-butyllithium (2.5M in hexanes, 4.08 mL, 10.2 mmol). The mixture was allowed to warm to 0° C. and stirred for 15 minutes. The mixture was recooled to −78° C. To this mixture was added the tetrahydrofuran solution of pyrimidin-5-ylmethyl 4-methylbenzenesulfonate via cannula; the resulting reaction mixture was allowed to warm to room temperature and was stirred for 18 hours. Water (50 mL) was added, and the mixture extracted with ethyl acetate (2×50 mL). The combined organic extracts were dried (Na$_2$SO$_4$), filtered and concentrated under reduced pressure. The residue was purified by column chromatography on silica gel Biotage 25S, eluting with 0-100% ethyl acetate/hexane to afford 3-methyl-3-(pyrimidin-5-ylmethyl)-1,3-dihydro-2H-indol-2-one as a white solid.

$^1$H NMR (CDCl$_3$): δ 8.97 (s, 1H), 8.29 (s, 2H), 7.88 (br s, 1H), 7.25 (d, 1H, J=7.3 Hz), 7.20 (m, 1H), 7.11 (m, 1H), 6.74 (d, 1H, J=7.8 Hz), 3.20 (d, 1H, J=13.5 Hz), 3.0 (d, 1H, J=13.5 Hz), 1.57 (s, 3H)
MS: m/e 240.19 (M+H)$^+$

Step 3: Preparation of 3-methyl-3-(pyrimidin-5-ylmethyl)-5-bromo-1,3-dihydro-2H-indol-2-one

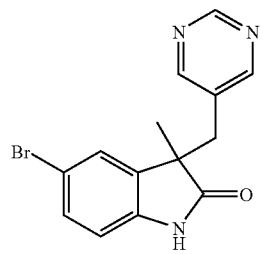

3-Methyl-3-(pyrimidin-5-ylmethyl)-1,3-dihydro-2H-indol-2-one (900 mg, 3.76 mmol) and N-bromosuccinimide (669 mg, 3.76 mmol) in N,N-dimethylformamide (20 mL) were stirred at room temperature for 3 days. The mixture was diluted with ethyl acetate (100 mL) and washed with water (100 mL). The organic layer was dried (MgSO$_4$), filtered and concentrated under reduced pressure. The residue was purified by preparative HPLC on Chiralpak AS, eluting with 25% isopropyl alcohol/CO$_2$, to afford the enantiomers of 3-methyl-3-(pyrimidin-5-ylmethyl)-5-bromo-1,3-dihydro-2H-indol-2-one. Enantiomer A was isolated as a white solid.

$^1$H NMR (CDCl$_3$): δ 8.99 (s, 1H), 8.33 (s, 2H), 8.15 (br s, 1H), 7.41 (s, 1H), 7.34 (dd, 1H, J=8.2, 1.8 Hz), 6.63 (d, 1H, J=8.2 Hz), 3.22 (d, 1H, J=13.5 Hz), 3.0 (d, 1H, J=13.7 Hz), 1.57 (s, 3H)
MS: m/e 318.0 (M+H)$^+$

Step 4: Preparation of 5-(3,4-difluorophenyl)-3-methyl-1-pyrimidin-2-yl-1,3-dihydro-2H-indol-2-one

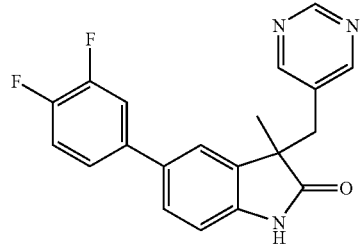

To enantiomer A of 3-methyl-3-(pyrimidin-5-ylmethyl)-5-bromo-1,3-dihydro-2H-indol-2-one (626 mg, 1.97 mmol), sodium carbonate (1043 mg, 9.84 mmol), [1,1'-bis(diphenylphosphino)ferrocene]dichloropalladium (II) (432 mg, 0.590 mmol) and 3,4-difluorophenylboronic acid (0.355 mL, 2.46 mmol) under nitrogen were added ethanol (5 mL) and toluene (5 mL). The mixture was stirred at 100° C. for 18 hours. The mixture was allowed to cool and the solvent was evaporated under reduced pressure. The residue was purified by column chromatography on silica gel Biotage 25M, eluting with 20-100% ethyl acetate/hexanes, to give 5-(3,4-difluorophenyl)-3-methyl-1-pyrimidin-2-yl-1,3-dihydro-2H-indol-2-one as a pale pink solid.

$^1$H NMR (CDCl$_3$): δ 9.00 (s, 1H), 8.33 (s, 2H), 7.57 (br s, 1H), 7.38 (m, 3H), 7.30 (m, 2H), 6.82 (d, 1H, J=7.7 Hz), 3.25 (d, 1H, J=13.5 Hz), 3.06 (d, 1H, J=13.5 Hz), 1.63 (s, 3H)

MS: m/e 352.43 (M+H)$^+$

Step 5: Preparation of 5-(3,4-difluorophenyl)-3-methyl-1-pyrimidin-2-yl-3-(pyrimidin-5-ylmethyl)-1,3-dihydro-2H-indol-2-one

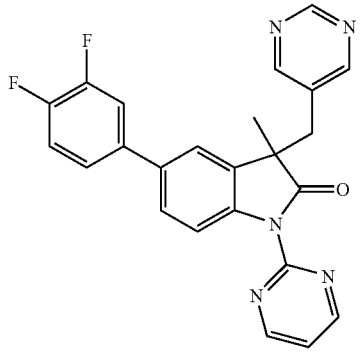

To a mixture of 5-(3,4-difluorophenyl)-3-methyl-1-pyrimidin-2-yl-1,3-dihydro-2H-indol-2-one, 2-bromopyrimidine (59.7 mg, 0.376 mmol), N,N'-dimethylethylenediamine (0.032 mL, 0.30 mmol), potassium carbonate (114 mg, 0.827 mmol) and copper (I) iodide (28.6 mg, 0.150 mmol) under nitrogen was added toluene (1 mL). The mixture was stirred at 100° C. for 18 hours. The mixture was allowed to cool to room temperature and diluted with ethyl acetate (30 mL). The mixture was washed with water (30 mL), dried (MgSO$_4$), filtered, and concentrated under reduced pressure. The residue was purified by preparative HPLC reverse phase (C-18), eluting with acetonitrile/water+0.1% TFA, to give the TFA salt of 5-(3,4-difluorophenyl)-3-methyl-1-pyrimidin-2-yl-3-(pyrimidin-5-ylmethyl)-1,3-dihydro-2H-indol-2-one as a white solid.

$^1$H NMR (CDCl$_3$): δ 8.99 (s, 1H), 8.87 (s, 1H), 8.37 (s, 2H), 7.61 (m, 1H), 7.31 (m, 3H), 7.29 (m, 4H), 3.39 (d, 1H, J=13.3 Hz), 3.14 (d, 1H, J=13.5 Hz), 1.63 (s, 3H)

MS: m/e 430.15 (M+H)$^+$

EXAMPLE 2

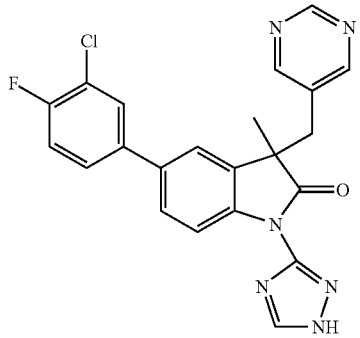

5-(3-chloro-4-fluorophenyl)-3-methyl-3-(pyrimidin-5-ylmethyl)-1-(1H-1,2,4-triazol-3-yl)-1,3-dihydro-2H-indol-2-one Step 1: Preparation of 5-(3-chloro-4-fluorophenyl)-3-methyl-1-pyrimidin-2-yl-1,3-dihydro-2H-indol-2-one

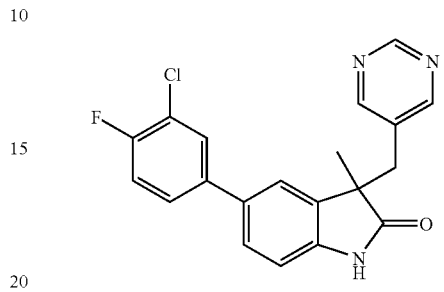

To 3-methyl-3-(pyrimidin-5-ylmethyl)-5-bromo-1,3-dihydro-2H-indol-2-one (860 mg, 2.70 mmol), sodium carbonate (745 mg, 7.03 mmol), tetrakis(triphenylphosphine)palladium(0) (469 mg, 0.41 mmol) and 3-chloro-4-fluorophenylboronic acid (471 mg, 2.70 mmol) under nitrogen were added dioxane (10 mL) and water (1 mL). The mixture was stirred at 100° C. for 18 hours. The mixture was allowed to cool and the solvent was evaporated under reduced pressure. The residue was purified by column chromatography on silica gel Biotage 25M, eluting with 0-4% dichloromethane/methanol, to give 5-(3-chloro-4-fluorophenyl)-3-methyl-1-pyrimidin-2-yl-1,3-dihydro-2H-indol-2-one as a cream solid.

$^1$H NMR (CDCl$_3$): δ 9.00 (s, 1H), 8.33 (s, 2H), 7.60 (m, 1H), 7.58 (br s, 1H), 7.43 (m, 3H), 7.23 (m, 1H), 6.81 (d, 1H, J=8.0 Hz), 3.25 (d, 1H, J=13.7 Hz), 3.06 (d, 1H, J=13.5 Hz) 1.63 (s, 3H)

MS: m/e 368.18 (M+H)$^+$

Step 2: Preparation of 5-(3-chloro-4-fluorophenyl)-3-methyl-3-(pyrimidin-5-ylmethyl)-1-(1-trityl-1,2,4-triazol-3-yl)-1,3-dihydro-2H-indol-2-one

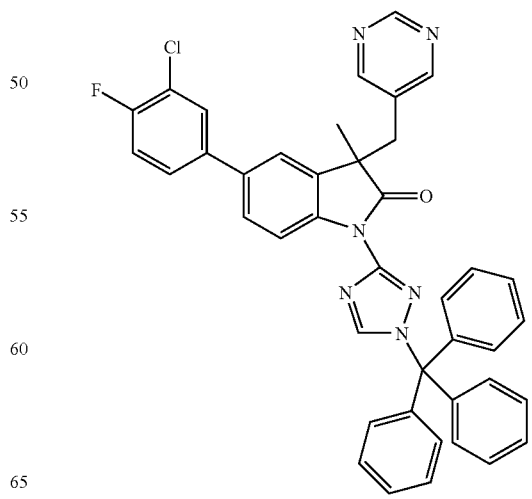

To 5-(3-chloro-4-fluorophenyl)-3-methyl-1-pyrimidin-2-yl-1,3-dihydro-2H-indol-2-one (648 mg, 1.76 mmol), 1-trityl-3-iodo-1,2,4-triazole (809 mg, 1.85 mmol, prepared using similar procedures as described in U.S. Pat. No. 5,393,732 incorporated herein by reference in its entirety. Potassium carbonate (1071 mg, 7.75 mmol), N,N'-dimethylethylenediamine (0.300 mL, 2.82 mmol) and copper (I) iodide (268 mg, 1.41 mmol) under nitrogen was added toluene (15 mL). The mixture was stirred at 100° C. for 18 hours. The mixture was cooled and the solvent was evaporated under reduced pressure. The residue was purified by column chromatography on silica gel Biotage 25S, eluting with 0-100% ethyl acetate/hexanes, to afford -(3-chloro-4-fluorophenyl)-3-methyl-1-pyrimidin-2-yl-1,3-dihydro-2H-indol-2-one as a white solid.

¹H NMR (CDCl₃): δ 8.98 (s, 1H), 8.34 (s, 2H), 8.04 (s, 1H), 7.56 (m, 1H), 7.41 (m, 1H), 7.30 (m, 18H), 7.05 (d, 1H, J=8.3 Hz), 3.31 (d, 1H, J=13.7 Hz), 3.12 (d, 1H, J=13.8 Hz) 1.59 (s, 3H)

MS: m/e 699.24 (M+Na)⁺

Step 3: 5-(3-chloro-4-fluorophenyl)-3-methyl-3-(pyrimidin-5-ylmethyl)-1-(1H-1,2,4-triazol-3-yl)-1,3-dihydro-2H-indol-2-one

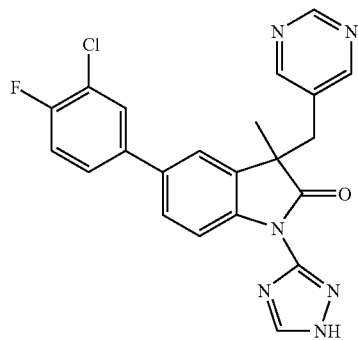

5-(3-chloro-4-fluorophenyl)-3-methyl-3-(pyrimidin-5-ylmethyl)-1-(1-trityl-1,2,4-triazol-3-yl)-1,3-dihydro-2H-indol-2-one (8.25 g, 12.2 mmol) in methanol (60 mL), dichloromethane (10 mL) and 1 N aqueous HCl solution (30 mL) was stirred at 50° C. for 1.5 hours. Most of the solvent was removed under reduced pressure. The residue was dissolved in dichloromethane and water (50 mL) was added. The pH of the mixture was adjusted to pH=7 with the addition of 1 N aqueous sodium hydroxide solution. The organic layer was separated and the aqueous layer further extracted with dichloromethane (2×100 mL). The organic extracts were combined, dried (MgSO₄), filtered and concentrated under reduced pressure. The residue was dissolved in dichloromethane and hexane was then slowly added. The product recrystallized over 3 days. The crystalline product was filtered, washed with 50% dichloromethane/hexanes and dried under reduced pressure. The filtrate was collected, concentrated under reduced pressure and purified by column chromatography on silica gel Biotage 40S, eluting with 40-100% ethyl acetate/hexanes, to give additional product. The product from crystallization and the product from column chromatography were combined, dissolved in acetonitrile/water and lyophilized to afford 5-(3-chloro-4-fluorophenyl)-3-methyl-3-(pyrimidin-5-ylmethyl)-1-(1H-1,2,4-triazol-3-yl)-1,3-dihydro-2H-indol-2-one as a white solid.

¹H NMR (CDCl₃): δ 9.00 (s, 1H), 8.32 (s, 2H), 7.97 (s, 1H), 7.64 (m, 1H), 7.57 (m, 1H), 7.45 (m, 2H), 7.26 (m, 3H), 3.34 (d, 1H, J=13.8 Hz), 3.20 (d, 1H, J=13.7 Hz) 1.74 (s, 3H)

MS: m/e 435.9 (M+Na)⁺

Using the procedures illustrated in Examples 1-2 with the appropriate modifications, reagent and substrates, the following additional examples were prepared.

TABLE 1

| Example | Structure | Chemical Name | Mass Spectral Data m/e (M + H), (M + 2 + H) |
|---|---|---|---|
| 3 | 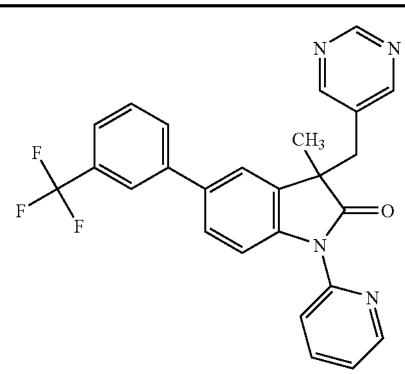 | 3-methyl-1-pyridin-2-yl-3-(pyrimidin-5-ylmethyl)-5-[3-(trifluoromethyl)phenyl]-1,3-dihydro-2H-indol-2-one | 461.12 |

TABLE 1-continued

| Example | Structure | Chemical Name | Mass Spectral Data m/e (M + H), (M + 2 + H) |
|---|---|---|---|
| 4 | 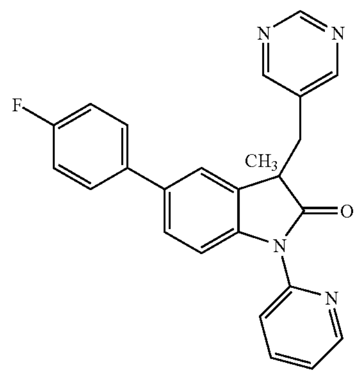 | 5-(4-fluorophenyl)-3-methyl-1-pyridin-2-yl-3-(pyrimidin-5-ylmethyl)-1,3-dihydro-2H-indol-2-one | 411.32 |
| 5 | 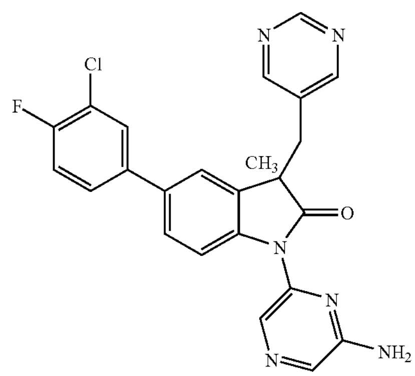 | 1-(6-aminopyrazin-2-yl)-5-(3-chloro-4-fluorophenyl)-3-methyl-3-(pyrimidin-5-ylmethyl)-1,3-dihydro-2H-indol-2-one | 461.17 |
| 6 | 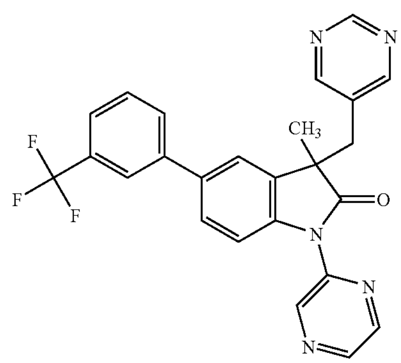 | 3-methyl-1-pyrazin-2-yl-3-(pyrimidin-5-ylmethyl)-5-[3-(trifluoromethyl)phenyl]-1,3-dihydro-2H-indol-2-one | 462.09 |
| 7 | 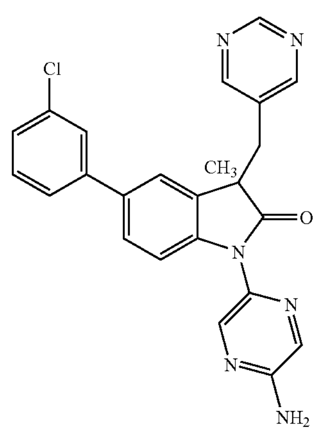 | 1-(5-aminopyrazin-2-yl)-5-(3-chlorophenyl)-3-methyl-3-(pyrimidin-5-ylmethyl)-1,3-dihydro-2H-indol-2-one | 442.68; 444.64 |

TABLE 1-continued

| Example | Structure | Chemical Name | Mass Spectral Data m/e (M + H), (M + 2 + H) |
|---|---|---|---|
| 8 | 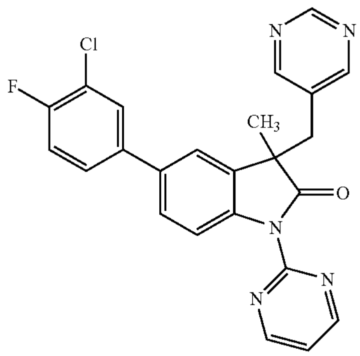 | 5-(3-chloro-4-fluorophenyl)-3-methyl-1-pyrimidin-2-yl-3-(pyrimidin-5-ylmethyl)-1,3-dihydro-2H-indol-2-one | 446.06, 448.04 |
| 9 | 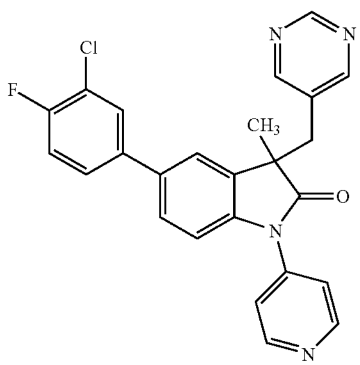 | 5-(3-chloro-4-fluorophenyl)-3-methyl-1-pyridin-4-yl-3-(pyrimidin-5-ylmethyl)-1,3-dihydro-2H-indol-2-one | 445.34, 447.18 |
| 10 | 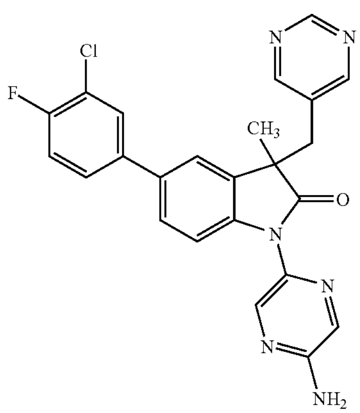 | 1-(5-aminopyrazin-2-yl)-5-(3-chloro-4-fluorophenyl)-3-methyl-3-(pyrimidin-5-ylmethyl)-1,3-dihydro-2H-indol-2-one | 461.32, 463.15 |
| 11 | 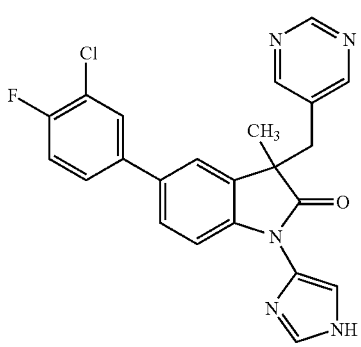 | 5-(3-chloro-4-fluorophenyl)-1-(1H-imidazol-4-yl)-3-methyl-3-(pyrimidin-5-ylmethyl)-1,3-dihydro-2H-indol-2-one | 434.38, 436.18 |

TABLE 1-continued

| Example | Structure | Chemical Name | Mass Spectral Data m/e (M + H), (M + 2 + H) |
|---|---|---|---|
| 12 | 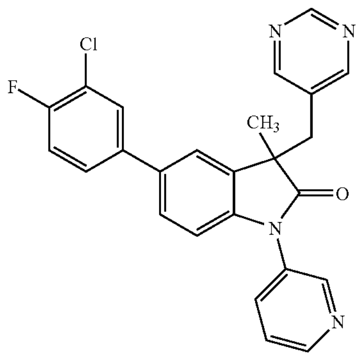 | 5-(3-chloro-4-fluorophenyl)-3-methyl-1-pyridin-3-yl-3-(pyrimidin-5-ylmethyl)-1,3-dihydro-2H-indol-2-one | 445.15, 447.13 |
| 13 | 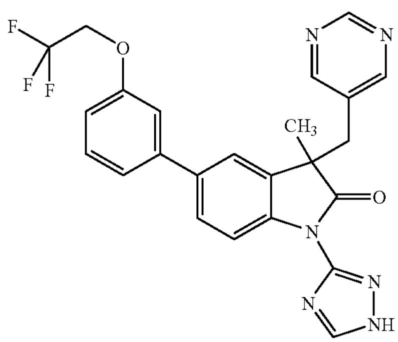 | 3-methyl-3-(pyrimidin-5-ylmethyl)-1-(1H-1,2,4-triazol-3-yl)-5-[3-(2,2,2-trifluoroethoxy)phenyl]-1,3-dihydro-2H-indol-2-one | 481.24 |
| 14 | 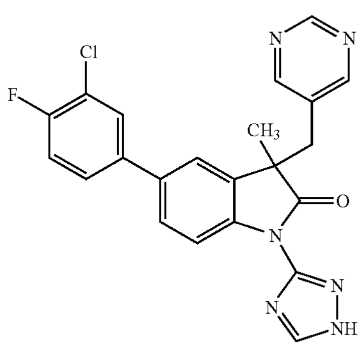 | 5-(3-chloro-4-fluorophenyl)-3-methyl-3-(pyrimidin-5-ylmethyl)-1-(1H-1,2,4-triazol-3-yl)-1,3-dihydro-2H-indol-2-one | 435.90 437.80 |
| 15 | 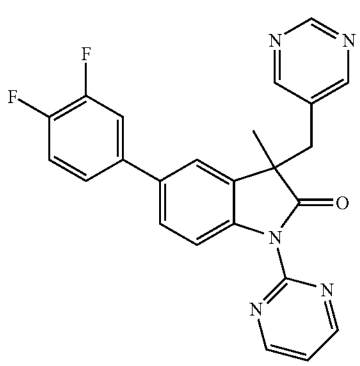 | 5-(3,4-difluorophenyl)-3-methyl-1-pyrimidin-2-yl-3-(pyrimidin-5-ylmethyl)-1,3-dihydro-2H-indol-2-one | 430.15 |

TABLE 1-continued

| Example | Structure | Chemical Name | Mass Spectral Data m/e (M + H), (M + 2 + H) |
|---|---|---|---|
| 16 | 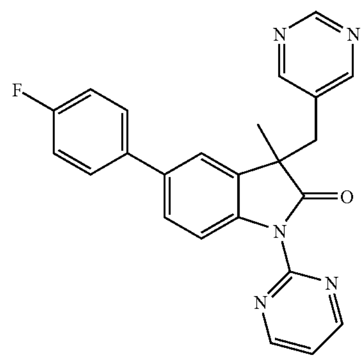 | 5-(4-fluorophenyl)-3-methyl-1-pyrimidin-2-yl-3-(pyrimidin-5-ylmethyl)-1,3-dihydro-2H-indol-2-one | 412.20 |
| 17 | 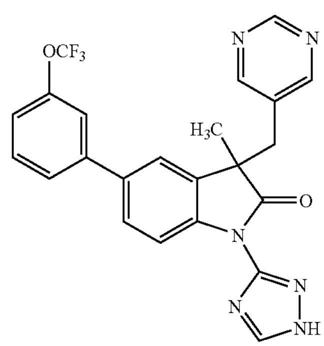 | 3-methyl-3-pyrimidin-5-ylmethyl-1-(1H-[1,2,4]triazol-3-yl)-5-(3-trifluoromethoxy-phenyl)-1,3-dihydro-indol-2-one | 467.7 |
| 18 | 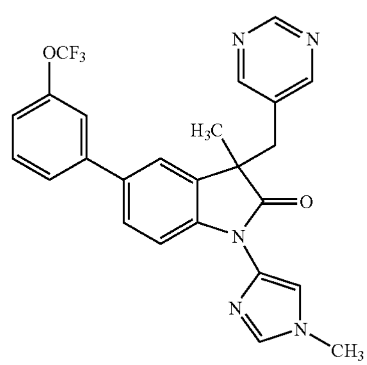 | 3-methyl-1-(1-methyl-1H-imidazol-4-yl)-3-pyrimidin-5-ylmethyl-5-(3-trifluoromethoxy-phenyl)-1,3-dihydro-indol-2-one | 480.6 |
| 19 | 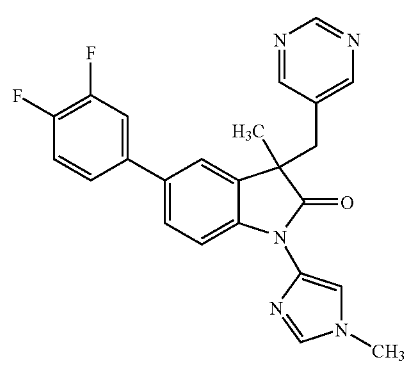 | 5-(3,4-difluoro-phenyl)-3-methyl-1-(1-methyl-1H-imidazol-4-yl)-3-pyrimidin-5-ylmethyl-1,3-dihydro-indol-2-one | 433.2 |

TABLE 1-continued

| Example | Structure | Chemical Name | Mass Spectral Data m/e (M + H), (M + 2 + H) |
|---|---|---|---|
| 20 | 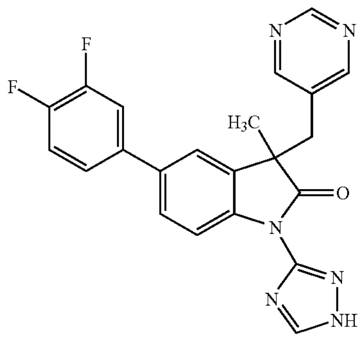 | 5-(3,4-difluoro-phenyl)-3-methyl-3-pyrimidin-5-ylmethyl-1-(1H-1,2,4-triazol-3-yl)-1,3-dihydro-indol-2-one | 419.3 |
| 21 | 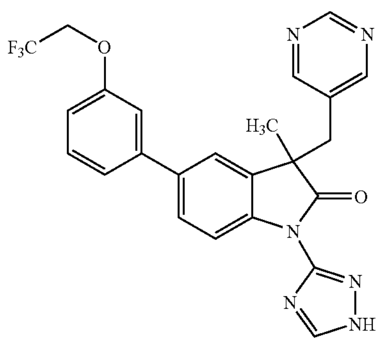 | 3-methyl-3-pyrimidin-5-ylmethyl-1-(1H-1,2,4-triazol-3-yl)-5-[3-(2,2,2-trifluoro-ethoxy)-phenyl]-1,3-dihydro-indol-2-one | 481.24 |
| 22 | 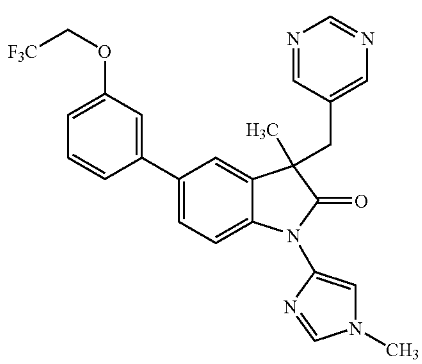 | 3-methyl-1-(1-methyl-1H-imidazol-4-yl)-3-pyrimidin-5-ylmethyl-5-[3-(2,2,2-trifluoro-ethoxy)-phenyl]-1,3-dihydro-indol-2-one | 494.06 |

TABLE 2

| Example | Structure | Chemical Name | Mass Spectral Data m/e (M + H), (M + 2 + H) |
|---|---|---|---|
| 23 | 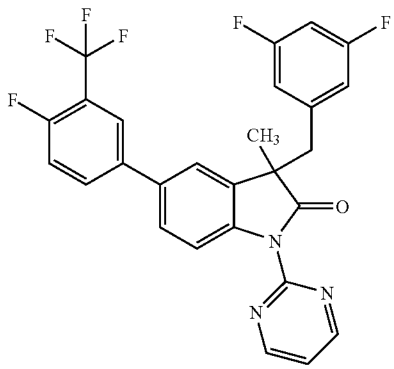 | 3-(3,5-difluorobenzyl)-5-[4-fluoro-3-(trifluoromethyl)phenyl]-3-methyl-1-pyrimidin-2-yl-1,3-dihydro-2H-indol-2-one | 514.13 |
| 24 | 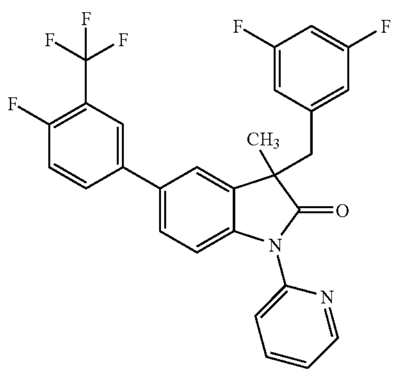 | 3-(3,5-difluorobenzyl)-5-[4-fluoro-3-(trifluoromethyl)phenyl]-3-methyl-1-pyridin-2-yl-1,3-dihydro-2H-indol-2-one | 513.28 |
| 25 | 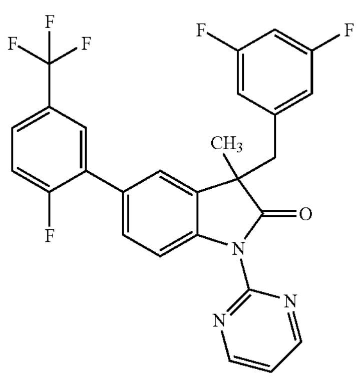 | 3-(3,5-difluorobenzyl)-5-[2-fluoro-5-(trifluoromethyl)phenyl]-3-methyl-1-pyrimidin-2-yl-1,3-dihydro-2H-indol-2-one | 514.13 |
| 26 | 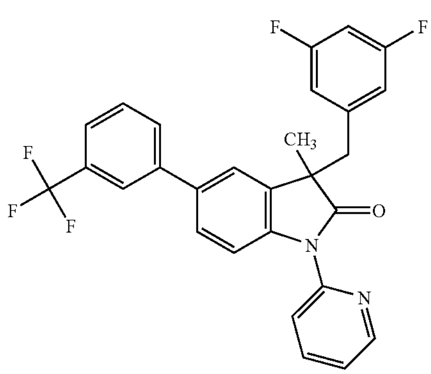 | 3-(3,5-difluorobenzyl)-3-methyl-1-pyridin-2-yl-5-[3-(trifluoromethyl)phenyl]-1,3-dihydro-2H-indol-2-one | 495.25 |

TABLE 2-continued

| Example | Structure | Chemical Name | Mass Spectral Data m/e (M + H), (M + 2 + H) |
|---|---|---|---|
| 27 | 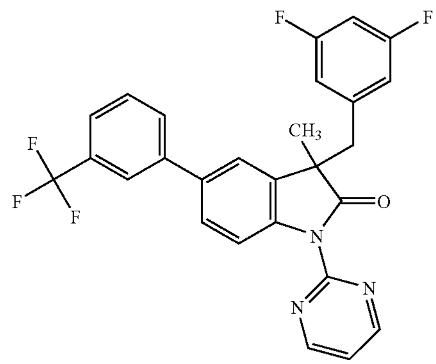 | 3-(3,5-difluorobenzyl)-3-methyl-1-pyrimidin-2-yl-5-[3-(trifluoromethyl)phenyl]-1,3-dihydro-2H-indol-2-one | 496.16 |
| 28 | 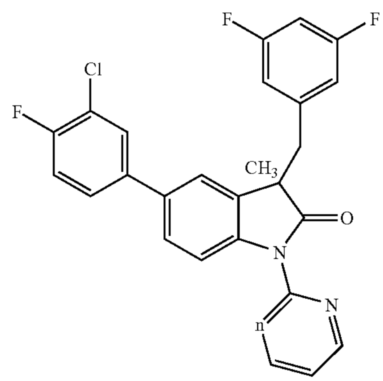 | 5-(3-chloro-4-fluorophenyl)-3-(3,5-difluorobenzyl)-3-methyl-1-pyrimidin-2-yl-1,3-dihydro-2H-indol-2-one | 480.23 482.21 |
| 29 | 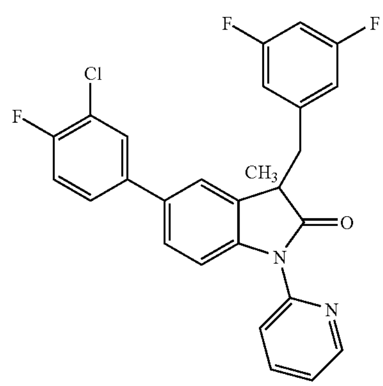 | 5-(3-chloro-4-fluorophenyl)-3-(3,5-difluorobenzyl)-3-methyl-1-pyridin-2-yl-1,3-dihydro-2H-indol-2-one | 479.20 481.22 |
| 30 | 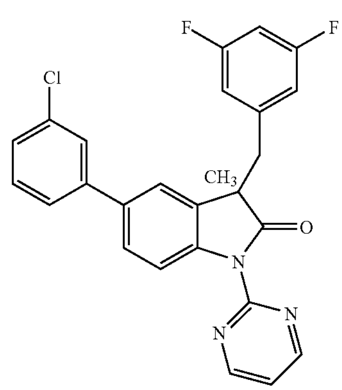 | 5-(3-chlorophenyl)-3-(3,5-difluorobenzyl)-3-methyl-1-pyrimidin-2-yl-1,3-dihydro-2H-indol-2-one | 462.28 464.27 |

TABLE 2-continued

| Example | Structure | Chemical Name | Mass Spectral Data m/e (M + H), (M + 2 + H) |
|---|---|---|---|
| 31 | 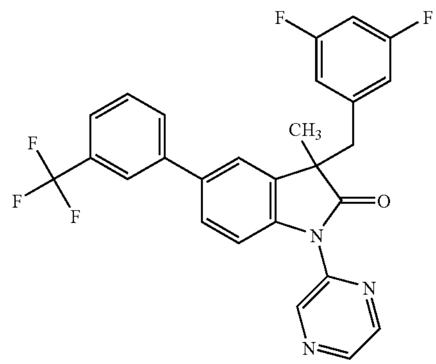 | 3-(3,5-difluorobenzyl)-3-methyl-1-pyrazin-2-yl-5-[3-(trifluoromethyl)phenyl]-1,3-dihydro-2H-indol-2-one | 495.64 |
| 32 | 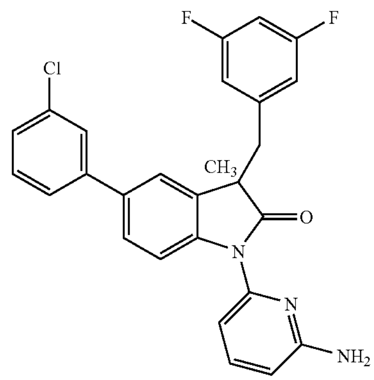 | 1-(6-aminopyridin-2-yl)-5-(3-chlorophenyl)-3-(3,5-difluorobenzyl)-3-methyl-1,3-dihydro-2H-indol-2-one | 476.22 478.20 |
| 33 | 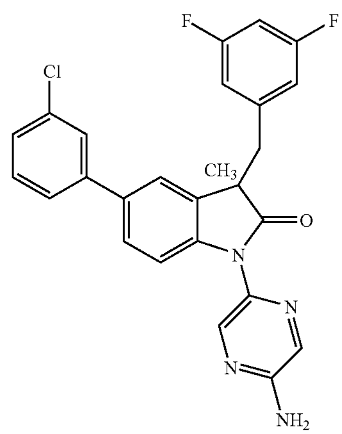 | 1-(5-aminopyrazin-2-yl)-5-(3-chlorophenyl)-3-(3,5-difluorobenzyl)-3-methyl-1,3-dihydro-2H-indol-2-one | 477.22 479.25 |
| 34 | 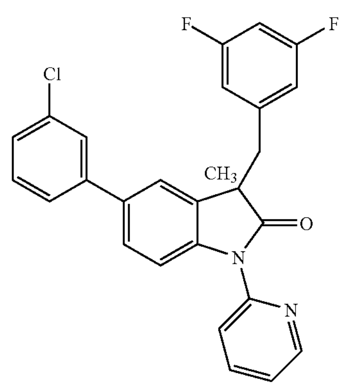 | 5-(3-chlorophenyl)-3-(3,5-difluorobenzyl)-3-methyl-1-pyridin-2-yl-1,3-dihydro-2H-indol-2-one | 461.30 463.28 |

TABLE 2-continued

| Example | Structure | Chemical Name | Mass Spectral Data m/e (M + H), (M + 2 + H) |
|---|---|---|---|
| 35 | 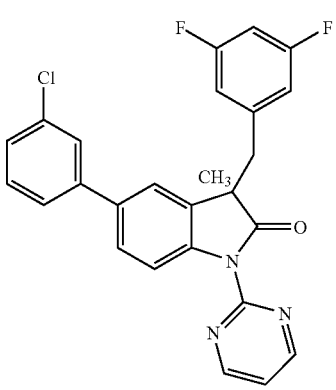 | 5-(3-chlorophenyl)-3-(3,5-difluorobenzyl)-3-methyl-1-pyrimidin-2-yl-1,3-dihydro-2H-indol-2-one | 462.29 464.27 |
| 36 | 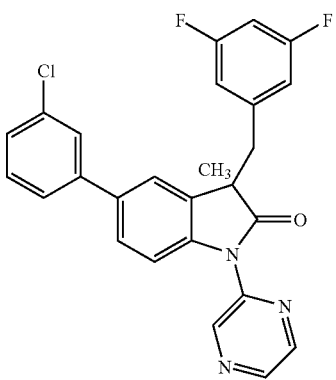 | 5-(3-chlorophenyl)-3-(3,5-difluorobenzyl)-3-methyl-1-pyrazin-2-yl-1,3-dihydro-2H-indol-2-one | 462.21 464.14 |
| 37 | 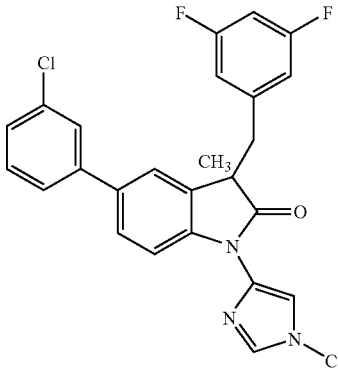 | 5-(3-chlorophenyl)-3-(3,5-difluorobenzyl)-3-methyl-1-(1-methyl-1H-imidazol-4-yl)-1,3-dihydro-2H-indol-2-one | 464.27 466.31 |
| 38 | 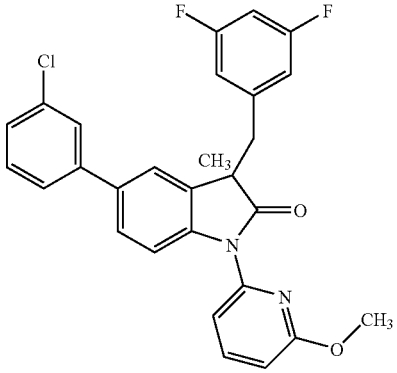 | 5-(3-chlorophenyl)-3-(3,5-difluorobenzyl)-1-(6-methoxypyridin-2-yl)-3-methyl-1,3-dihydro-2H-indol-2-one | 491.25 493.27 |

TABLE 2-continued

| Example | Structure | Chemical Name | Mass Spectral Data m/e (M + H), (M + 2 + H) |
|---|---|---|---|
| 39 | 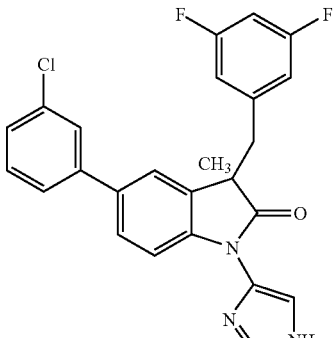 | 5-(3-chlorophenyl)-3-(3,5-difluorobenzyl)-1-(1H-imidazol-4-yl)-3-methyl-1,3-dihydro-2H-indol-2-one | 449.88 451.81 |
| 40 | 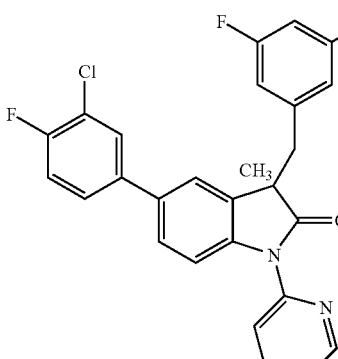 | 5-(3-chloro-4-fluorophenyl)-3-(3,5-difluorobenzyl)-3-methyl-1-pyridin-2-yl-1,3-dihydro-2H-indol-2-one | 479.40 481.42 |
| 41 | 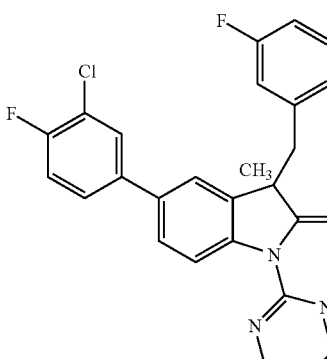 | 5-(3-chloro-4-fluorophenyl)-3-(3,5-difluorobenzyl)-3-methyl-1-pyrimidin-2-yl-1,3-dihydro-2H-indol-2-one | 480.41 |
| 42 | 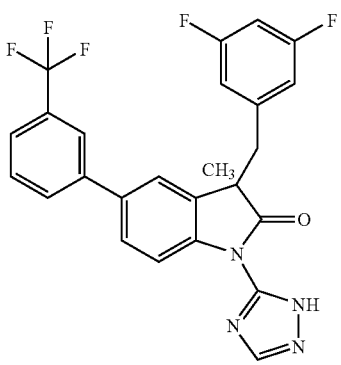 | 3-(3,5-difluorobenzyl)-3-methyl-1-(1H-1,2,4-triazol-5-yl)-5-[3-(trifluoromethyl)phenyl]-1,3-dihydro-2H-indol-2-one | 485.38 |

TABLE 2-continued

| Example | Structure | Chemical Name | Mass Spectral Data m/e (M + H), (M + 2 + H) |
|---|---|---|---|
| 43 | 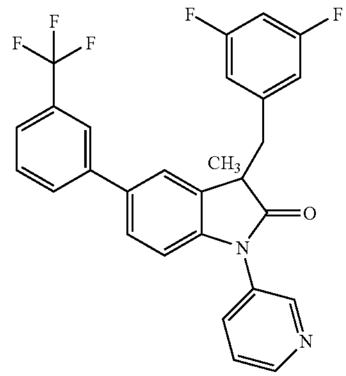 | 3-(3,5-difluorobenzyl)-3-methyl-1-pyridin-3-yl-5-[3-(trifluoromethyl)phenyl]-1,3-dihydro-2H-indol-2-one | 495.47 |
| 44 | 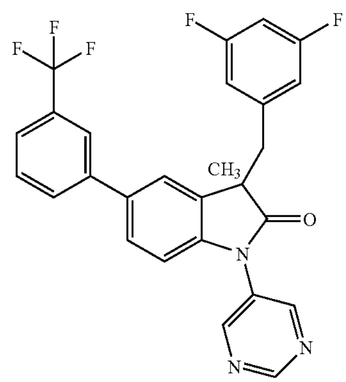 | 3-(3,5-difluorobenzyl)-3-methyl-1-pyrimidin-5-yl-5-[3-(trifluoromethyl)phenyl]-1,3-dihydro-2H-indol-2-one | 496.40 |
| 45 | 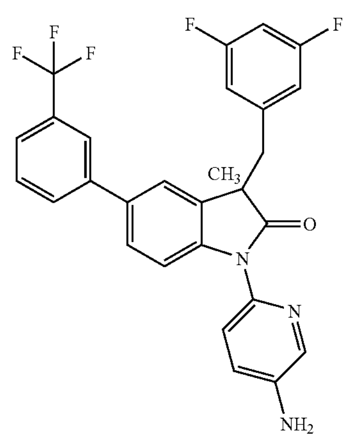 | 1-(5-aminopyridin-2-yl)-3-(3,5-difluorobenzyl)-3-methyl-5-[3-(trifluoromethyl)phenyl]-1,3-dihydro-2H-indol-2-one | 510.41 |

TABLE 2-continued

| Example | Structure | Chemical Name | Mass Spectral Data m/e (M + H), (M + 2 + H) |
|---|---|---|---|
| 46 | 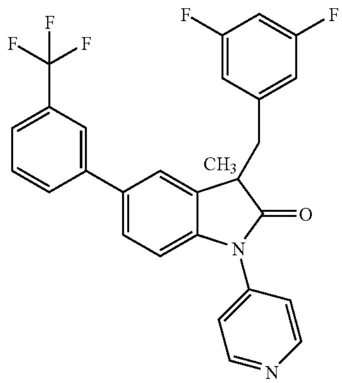 | 3-(3,5-difluorobenzyl)-3-methyl-1-pyridin-4-yl-5-[3-(trifluoromethyl)phenyl]-1,3-dihydro-2H-indol-2-one | 495.41 |
| 47 | 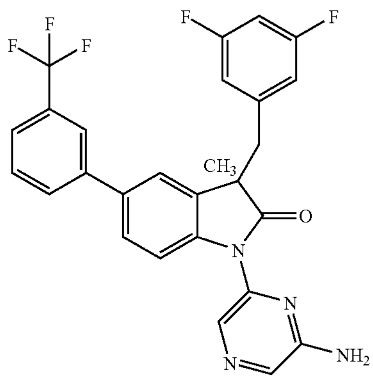 | 1-(6-aminopyrazin-2-yl)-3-(3,5-difluorobenzyl)-3-methyl-5-[3-(trifluoromethyl)phenyl]-1,3-dihydro-2H-indol-2-one | 511.43 |
| 48 | 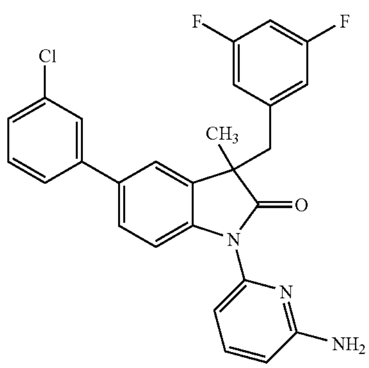 | 1-(6-aminopyridin-2-yl)-5-(3-chlorophenyl)-3-(3,5-difluorobenzyl)-3-methyl-1,3-dihydro-2H-indol-2-one | 476.16 478.06 |
| 49 | 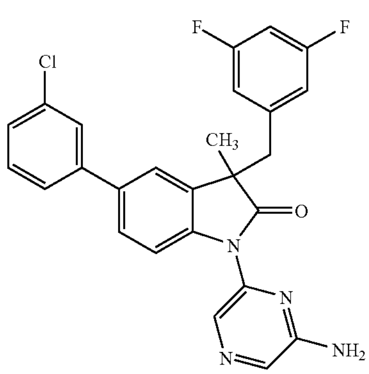 | 1-(6-aminopyrazin-2-yl)-5-(3-chlorophenyl)-3-(3,5-difluorobenzyl)-3-methyl-1,3-dihydro-2H-indol-2-one | 477.15 479.03 |

TABLE 2-continued

| Example | Structure | Chemical Name | Mass Spectral Data m/e (M + H), (M + 2 + H) |
|---|---|---|---|
| 50 | 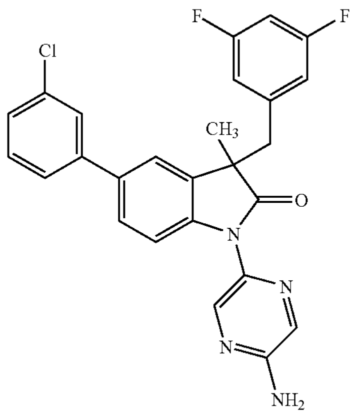 | 1-(5-aminopyrazin-2-yl)-5-(3-chlorophenyl)-3-(3,5-difluorobenzyl)-3-methyl-1,3-dihydro-2H-indol-2-one | 477.15 479.05 |
| 51 | 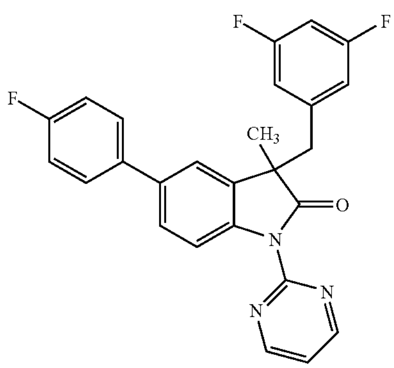 | 3-(3,5-difluorobenzyl)-5-(4-fluorophenyl)-3-methyl-1-pyrimidin-2-yl-1,3-dihydro-2H-indol-2-one | 446.21 |
| 52 | 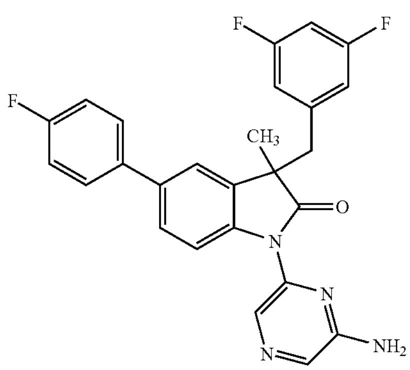 | 1-(6-aminopyrazin-2-yl)-3-(3,5-difluorobenzyl)-5-(4-fluorophenyl)-3-methyl-1,3-dihydro-2H-indol-2-one | 461.10 |
| 53 | 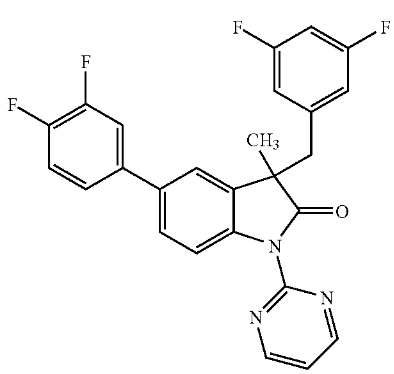 | 3-(3,5-difluorobenzyl)-5-(3,4-difluorophenyl)-3-methyl-1-pyrimidin-2-yl-1,3-dihydro-2H-indol-2-one | 463.36 |

TABLE 2-continued

| Example | Structure | Chemical Name | Mass Spectral Data m/e (M + H), (M + 2 + H) |
|---|---|---|---|
| 54 | 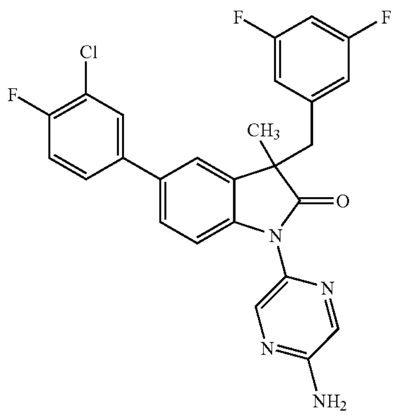 | 1-(5-aminopyrazin-2-yl)-5-(3-chloro-4-fluorophenyl)-3-(3,5-difluorobenzyl)-3-methyl-1,3-dihydro-2H-indol-2-one | 495.28 497.21 |
| 55 | 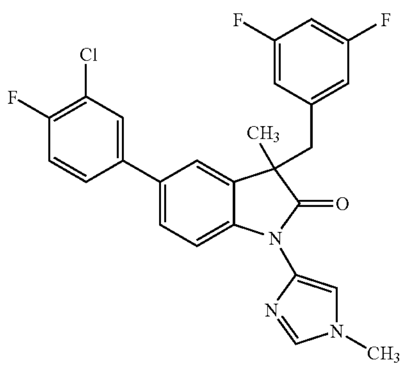 | 5-(3-chloro-4-fluorophenyl)-3-(3,5-difluorobenzyl)-3-methyl-1-(1-methyl-1H-imidazol-4-yl)-1,3-dihydro-2H-indol-2-one | 482.55 484.23 |
| 56 | 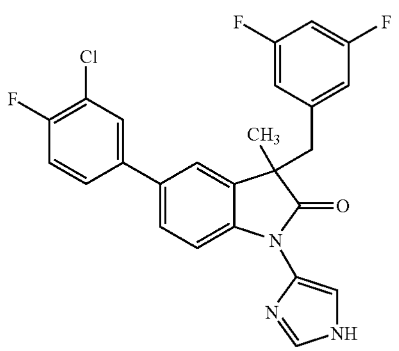 | 5-(3-chloro-4-fluorophenyl)-3-(3,5-difluorobenzyl)-1-(1H-imidazol-4-yl)-3-methyl-1,3-dihydro-2H-indol-2-one | 468.40 470.24 |
| 57 | 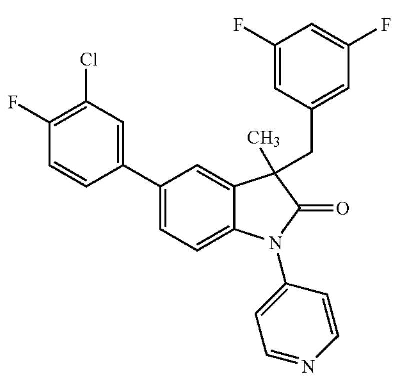 | 5-(3-chloro-4-fluorophenyl)-3-(3,5-difluorobenzyl)-3-methyl-1-pyridin-4-yl-1,3-dihydro-2H-indol-2-one | 479.37 481.27 |

TABLE 2-continued

| Example | Structure | Chemical Name | Mass Spectral Data m/e (M + H), (M + 2 + H) |
|---|---|---|---|
| 58 | 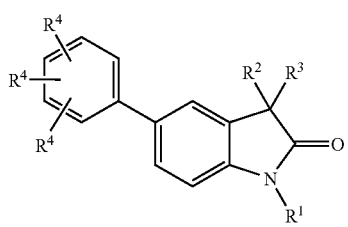 | 5-(3-chloro-4-fluorophenyl)-3-(3,5-difluorobenzyl)-1-(1-isopropyl-1H-imidazol-4-yl)-3-methyl-1,3-dihydro-2H-indol-2-one | 510.25 512.34 |
| 59 | 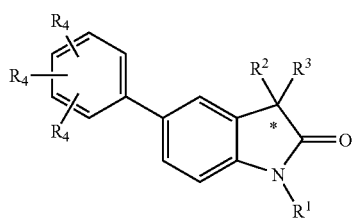 | 3-(3,5-difluorobenzyl)-5-(3,4-difluorophenyl)-3-methyl-1-pyrimidin-2-yl-1,3-dihydro-2H-indol-2-one | 464.39 |

What is claimed is:

1. A compound of structural formula I:

(I)

or pharmaceutically acceptable salts thereof and individual enantiomers and diastereomers thereof: wherein:

$R^1$ = aryl or heteroaryl, optionally substituted with 1-3 substituents consisting of: $C_{1-6}$ alkyl, $C_{1-4}$-fluoroalkyl, $C_{6-10}$-aryl, or $C_{6-10}$heteroaryl, F, Cl, Br, CN, $OR^5$, $NR^5R^6$, $SO_2R^5$, $SO_2NR^5R^6$, $NR^5SO_2R^6$, $CO_2R^5$, $CONR^5R^6$;

$R^2$ = $C_{1-6}$ alkyl, $C_{1-6}$ fluoroalkyl;

$R^3$ = $(CH_2)_n$ aryl or $(CH_2)_n$ heteroaryl, wherein each aryl or heteroaryl is optionally substituted with 1-3 substituents consisting of: $C_{1-6}$ alkyl, $C_{1-4}$-fluoroalkyl, $C_{6-10}$-aryl, $C_{6-10}$ heteroaryl, F, Cl, Br, CN, $OR^5$, $NR^5R^6$, $SO_2R^5$, $SO_2NR^5R^6$, $NR^5SO_2R^6$, $CO_2R^5$, $CONR^5R^6$;

each $R^4$ is independently selected from H, $C_{1-6}$ alkyl, $C_{1-4}$-fluoroalkyl, aryl, heteroaryl, F, Cl, Br, CN, $OR^5$, $NR^5R^6$, $SO_2R^5$, $SO_2NR^5R^6$, $NR^5SO_2R^6$, $CO_2R^5$, and $CONR^5R^6$;

$R^5$ and $R^6$ are each independently selected from H, $C_{1-6}$ alkyl, $C_{1-4}$-fluoroalkyl, $C_{3-7}$-cycloalkyl, $C_{6-10}$-aryl, and $C_{6-10}$heteroaryl or $R^5$ and $R^6$ join to form a 3-7 member carbocyclic or heterocyclic ring and n = 0-6.

2. The compound according to claim 1 wherein $R^2$ is methyl, and $R^3$ is a methylene-linked aryl or heteroaryl.

3. The compound according to claim 1 represented by:

wherein the stereocenter depicted by "*" in formula I is in the S or R stereochemical configuration.

4. The compound according to claim 1 wherein $R^1$ is an aryl optionally substituted.

5. The compound according to claim 3 represented by structural formula Ib

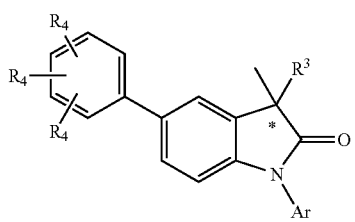

wherein R³ is a methylene-linked aryl or heteroaryl substituent and the stereocenter depicted by "*" in formula Ib is in the R stereochemical configuration and Ar is selected from the group consisting of phenyl, napthyl, and biphenyl.

6. The compound according to claim 5 wherein R³ is selected from the group consisting of a methylene-linked phenyl, napthyl, tetrahydronapthyl, indanyl, biphenyl, furyl, imidazolidinyl, imidazolinyl, imidazolyl, indolinyl, indolyl, isoquinolinyl, morpholinyl, oxazolyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, and quinolinyl.

7. The compound according to claim 3 wherein R¹ is a heteroaryl, optionally substituted.

8. The compound according to claim 7 represented by structural formula Ic

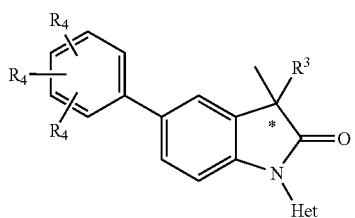

wherein R³ is a methylene-linked aryl or heteroaryl and the stereocenter depicted by "*" in formula Ic is in the R stereochemical configuration and Het is selected from the group consisting of thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, triazolyl, oxazolyl, thiazolyl, and isoxazoyl.

9. The compound according claim 8 wherein R³ is selected from the group consisting of methylene-linked phenyl, napthyl, tetrahydronapthyl, indanyl, biphenyl, furyl, imidazolidinyl, imidazolinyl, imidazolyl, indolinyl, indolyl, isoquinolinyl, morpholinyl, oxazolyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, and quinolinyl.

10. The compound according to claim 1 wherein R¹ is heteroaryl and R³ is a methylene-linked heteroaryl.

11. The compound according to claim 10 wherein the heteroaryl is selected from the group consisting of thienyl, benzothienyl, furyl, benzofuryl, dibenzofuryl, pyrrolyl, imidazolyl, pyrazoiyl, pyridyl, pyrazinyl, pyrimidinyl, indolyl, quinolyl, isoquinolyl, quinoxalinyl, tetrazolyl, triazolyl, oxazolyl, thiazolyl, and isoxazoyl and for R³ n is 1 and the heteroaryl is selected from the group consisting of furyl, imidazolidinyl, imidazolinyl, imidazolyl, indolinyl, indolyl, isoquinolinyl, morpholinyl, oxazolyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, and quinolinyl.

12. A pharmaceutical composition comprising an inert carrier and an effective amount of a compound according to claim 1.

13. A compound which is:
   3-methyl-1-pyridin-2-yl-3-(pyrimidin-5-ylmethyl)-5-[3-(trifluoromethyl)phenyl]-1,3-dihydro-2H-indol-2-one,
   5-(4-fluorophenyl)-3-methyl-1-pyridin-2-yl-3-(pyrimidin-5-ylmethyl)-1,3-dihydro-2H-indol-2-one,
   1-(6-aminopyrazin-2-yl)-5-(3-chloro-4-fluorophenyl)-3-methyl-3-(pyrimidin-5-ylmethyl)-1,3-dihydro-2H-indol-2-one,
   3-methyl-1-pyrazin-2-yl-3-(pyrimidin-5-ylmethyl)-5-[3-(trifluoromethyl)phenyl]-1,3-dihydro-2H-indol-2-one,
   1-(5-aminopyrazin-2-yl)-5-(3-chlorophenyl)-3-methyl-3-(pyrimidin-5-ylmethyl)-1,3-dihydro-2H-indol-2-one,
   5-(3-chloro-4-fluorophenyl)-3-methyl-1-pyrimidin-2-yl-3-(pyrimidin-5-ylmethyl)-1,3-dihydro-2H-indol-2-one,
   5-(3-chloro-4-fluorophenyl)-3-methyl-1-pyridin-4-yl-3-(pyrimidin-5-ylmethyl)-1,3-dihydro-2H-indol-2-one,
   1-(5-aminopyrazin-2-yl)-5-(3-chloro-4-fluorophenyl)-3-methyl-3-(pyrimidin-5-ylmethyl)-1,3-dihydro-2H-indol-2-one,
   5-(3-chloro-4-fluorophenyl)-1-(1H-imidazol-4-yl)-3-methyl-3-(pyrimidin-5-ylmethyl)-1,3-dihydro-2H-indol-2-one,
   5-(3-chloro-4-fluorophenyl)-3-methyl-1-pyridin-3-yl-3-(pyrimidin-5-ylmethyl)-1,3-dihydro-2H-indol-2-one,
   3-methyl-3-(pyrimidin-5-ylmethyl)-1-(1H-1,2,4-triazol-3-yl)-5-[3-(2,2,2-trifluoroethoxy)-phenyl]-1,3-dihydro-2H-indol-2-one,
   5-(3-chloro-4-fluorophenyl)-3-methyl-3-(pyrimidin-5-ylmethyl)-1-(1H-1,2,4-triazol-3-yl)-1,3-dihydro-2H-indol-2-one,
   5-(3,4-difluorophenyl)-3-methyl-1-pyrimidin-2-yl-3-(pyrimidin-5-ylmethyl)-1,3-dihydro-2H-indol-2-one,
   5-(4-fluorophenyl)-3-methyl-1-pyrimidin-2-yl-3-(pyrimidin-5-ylmethyl)-1,3-dihydro-2H-indol-2-one,
   3-(3,5-difluorobenzyl)-5-[4-fluoro-3-(trifluoromethyl)phenyl]-3-methyl-1-pyrimidin-2-yl-1,3-dihydro-2H-indol-2-one,
   3-(3,5-difluorobenzyl)-5-[4-fluoro-3-(trifluoromethyl)phenyl]-3-methyl-1-pyridin-2-yl-1,3-dihydro-2H-indol-2-one,
   3-(3,5-difluorobenzyl)-5-[2-fluoro-5-(trifluoromethyl)phenyl]-3-methyl-1-pyrimidin-2-yl-1,3-dihydro-2H-indol-2-one,
   3-(3,5-difluorobenzyl)-3-methyl-1-pyridin-2-yl-5-[3-(trifluoromethyl)phenyl]-1,3-dihydro-2H-indol-2-one,
   3-(3,5-difluorobenzyl)-3-methyl-1-pyrimidin-2-yl-5-[3-(trifluoromethyl)phenyl]-1,3-dihydro-2H-indol-2-one,
   5-(3-chloro-4-fluorophenyl)-3-(3,5-difluorobenzyl)-3-methyl-1-pyrimidin-2-yl-1,3-dihydro-2H-indol-2-one,
   5-(3-chloro-4-fluorophenyl)-3-(3,5-difluorobenzyl)-3-methyl-1-pyridin-2-yl-1,3-dihydro-2H-indol-2-one,
   5-(3-chlorophenyl)-3-(3,5-difluorobenzyl)-3-methyl-1-pyrimidin-2-yl-1,3-dihydro-2H-indol-2-one,
   5-(3-chlorophenyl)-3-(3,5-difluorobenzyl)-1,3-dimethyl-1,3-dihydro-2H-indol-2-one,
   3-(3,5-difluorobenzyl)-3-methyl-1-pyrazin-2-yl-5-[3-(trifluoromethyl)phenyl]-1,3-dihydro-2H-indol-2-one,
   3-(3,5-difluorobenzyl)-1,3-dimethyl-5-[3-(trifluoromethyl)phenyl]-1,3-dihydro-2H-indol-2one, 1-(6-aminopyridin-2-yl)-5-(3-chlorophenyl)-3-(3,5-difluorobenzyl)-3-methyl-1,3-dihydro-2H-indol-2-one,
1-(5-aminopyrazin-2-yl)-5-(3-chlorophenyl)-3-(3,5-difluorobenzyl)-3-methyl-1,3-dihydro-2H-indol-2-one,
5-(3-chlorophenyl)-3-(3,5-difluorobenzyl)-3-methyl-1-pyridin-2-yl-1,3-dihydro-2H-indol-2-one,
5-(3-chlorophenyl)-3-(3,5-difluorobenzyl)-3-methyl-1-pyrimidin-2-yl-1,3-dihydro-2H-indol-2-one,
5-(3-chlorophenyl)-3-(3,5-difluorobenzyl)-3-methyl-1-pyrazin-2-yl-1,3-dihydro-2H-indol-2-one,
5-(3-chlorophenyl)-3-(3,5-difluorobenzyl)-1-(6-methoxypyridin-2-yl)-3-methyl-1,3-dihydro-2H-indol-2-one,
5-(3-chlorophenyl)-3-(3,5-difluorobenzyl)-1-(1H-imidazol-4-yl)-3-methyl-1,3-dihydro-2H-indol-2-one,
5-(3-chloro-4-fluorophenyl)-3-(3,5-difluorobenzyl)-3-methyl-1-pyridin-2-yl-1,3-dihydro-2H-indol-2-one,
5-(3-chloro-4-fluorophenyl)-3-(3,5-difluorobenzyl)-3-methyl-1-pyrimidin-2-yl-1,3-dihydro-2H-indol-2-one,
3-(3,5-difluorobenzyl)-3-methyl-1-(1H-1,2,4-triazol-5-yl)-5-[3-(trifluoromethyl)phenyl]-1,3-dihydro-2H-indol-2-one,
3-(3,5-difluorobenzyl)-3-methyl-1-pyridin-3-yl-5-[3-(trifluoromethyl)phenyl]-1,3-dihydro-2H-indol-2-one,
3-(3,5-difluorobenzyl)-3-methyl-1-pyrimidin-5-yl-5-[3-(trifluoromethyl)phenyl]-1,3-dihydro-2H-indol-2-one,
1-(5-aminopyridin-2-yl)-3-(3,5-difluorobenzyl)-3-methyl-5-[3-(trifluoromethyl)phenyl]-1,3-dihydro-2H-indol-2-one,
3-(3,5-difluorobenzyl)-3-methyl-1-pyridin-4-yl-5-[3-(trifluoromethyl)phenyl]-1,3-dihydro-2H-indol-2-one,
1-(6-aminopyrazin-2-yl)-3-(3,5-difluorobenzyl)-3-methyl-5-[3-(trifluoromethyl)phenyl]-1,3-dihydro-2H-indol-2-one,
1-(6-aminopyridin-2-yl)-5-(3-chlorophenyl)-3-(3,5-difluorobenzyl)-3-methyl-1,3-dihydro-2H-indol-2-one,
1-(6-aminopyrazin-2-yl)-5-(3-chlorophenyl)-3-(3,5-difluorobenzyl)-3-methyl-1,3-dihydro-2H-indol-2-one,
1-(5-aminopyrazin-2-yl)-5-(3-chlorophenyl)-3-(3,5-difluorobenzyl)-3-methyl-1,3-dihydro-2H-indol-2-one,
3-(3,5-difluorobenzyl)-5-(4-fluorophenyl)-3-methyl-1-pyrimidin-2-yl-1,3-dihydro-2H-indol-2-one,
1-(6-aminopyrazin-2-yl)-3-(3,5-difluorobenzyl)-5-(4-fluorophenyl)-3-methyl-1,3-dihydro-2H-indol-2-one,
3-(3,5-difluorobenzyl)-5-(3,4-difluorophenyl)-3-methyl-1-pyrimidin-2-yl-1,3-dihydro-2H-indol-2-one,
1-(5-aminopyrazin-2-yl)-5-(3-chloro-4-fluorophenyl)-3-(3,5-difluorobenzyl)-3-methyl-1,3-dihydro-2H-indol-2-one,
5-(3-chloro-4-fluorophenyl)-3-(3,5-difluorobenzyl)-1-(1H-imidazol-4-yl)-3-methyl-1,3-dihydro-2H-indol-2-one,
5-(3-chloro-4-fluorophenyl)-3-(3,5-difluorobenzyl)-3-methyl-1-pyridin-4-yl-1,3-dihydro-2H-indol-2-one,
3-(3,5-difluorobenzyl)-5-(3,4-difluorophenyl)-3-methyl-1-pyrimidin-2-yl-1,3-dihydro-2H-indol-2-one,
3-methyl-3-pyrimidin-5-ylmethyl-1-(1H-[1,2,4]triazol-3-yl)-5-(3-trifluoromethoxy-phenyl)-1,3-dihydro-indol-2-one,
3-methyl-1-(1-methyl-1H-imidazol-4-yl)-3-pyrimidin-5-ylmethyl-5-(3-trifluoromethoxy-phenyl)-1,3-dihydro-indol-2-one,
5-(3,4-difluoro-phenyl)-3-methyl-1-(1-methyl-1H-imidazol-4-yl)-3-pyrimidin-5-ylmethyl-1,3-dihydro-indol-2-one,
5-(3,4-difluoro-phenyl)-3-methyl-3-pyrimidin-5-ylmethyl-1-(1H-1,2,4-triazol-3-yl)-1,3-dihydro-indol-2-one,
3-methyl-3-pyrimidin-5-ylmethyl-1-(1H-1,2,4-triazol-3-yl)-5-[3-(2,2,2-trifluoro-ethoxy)-phenyl]-1,3-dihydro-indol-2-one,
3-methyl-1-(1-methyl-1H-imidazol-4-yl)-3-pyrimidin-5-ylmethyl-5-[3-(2,2,2-trifluoro-ethoxy)-phenyl]-1,3-dihydro-indol-2-one, or pharmaceutically acceptable salts thereof and individual enantiomers and diastereomers thereof.

14. A method for treating chronic or acute pain in a mammalian patient in need thereof comprising administering to said patient a therapeutically effective amount, or a prophylactically effective amount, of a compound according to claim 1, or a pharmaceutically acceptable salt thereof.

15. A method for treating epilepsy in a mammalian patient in need thereof, which comprises administering to the patient a therapeutically effective amount of the compound of claim 1, or a pharmaceutically acceptable salt thereof.

* * * * *